US009139575B2

(12) United States Patent
Lee et al.

(10) Patent No.: US 9,139,575 B2
(45) Date of Patent: Sep. 22, 2015

(54) BROAD SPECTRUM ANTIVIRAL AND ANTIPARASITIC AGENTS

(75) Inventors: Benhur Lee, Los Angeles, CA (US); Michael E. Jung, Los Angeles, CA (US); Jihye Lee, Los Angeles, CA (US); Frederic Vigant, Hollywood, CA (US); Peter J. Bradley, Los Angeles, CA (US); Michael C. Wolf, Washington, DC (US); Bettina E. Hajagos, Corona Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/640,732

(22) PCT Filed: Apr. 13, 2011

(86) PCT No.: PCT/US2011/032336

§ 371 (c)(1), (2), (4) Date: Oct. 11, 2012

(87) PCT Pub. No.: WO2011/130419

PCT Pub. Date: Oct. 20, 2011

(65) Prior Publication Data

US 2013/0028966 A1 Jan. 31, 2013

Related U.S. Application Data

(60) Provisional application No. 61/467,912, filed on Mar. 25, 2011, provisional application No. 61/323,823, filed on Apr. 13, 2010.

(51) Int. Cl.

*C07D 417/06* (2006.01)
*C07D 405/06* (2006.01)
*C07D 413/06* (2006.01)

(52) U.S. Cl.

CPC ............ *C07D 413/06* (2013.01); *C07D 405/06* (2013.01)

(58) Field of Classification Search

None

See application file for complete search history.

(56) References Cited

U.S. PATENT DOCUMENTS 4,150,144 A 4/1979 Eckhardt et al.
4,255,740 A 3/1981 Ferrie (Continued)

FOREIGN PATENT DOCUMENTS

WO WO 2004/028441 A2 4/2004
WO WO 2004/073594 A2 9/2004
WO WO 2011/075784 * 6/2011

OTHER PUBLICATIONS

Williams et al. Foye's Principles of Medicinal Chemistry, 5th edition, pp. 59-63, 2002.*

Bulic, B. et al., "Rhodanine-Based Tau Aggregation Inhibitors in Cell Models of Tauopathy," Angewandte Chemie, International Edition, Dec. 4, 2007, pp. 9215-9219, vol. 46, No. 48.

Carter, P. H. et al., "Photochemically Enhanced Binding of Small Molecules to the Tumor Necrosis Factor Receptor-1 Inhibits the Binding of TNF-α," Proceedings of the National Academy of Sciences of the United States of America, Oct. 9, 2001, pp. 11879-11884, vol. 98, No. 21.

Cheng, C-Y. et al., "Guaranteeing Quality of Service in Interactive Video-on-Demand Servers," IEEE Transactions on Consumer Electronics, May 1999, pp. 396-407, vol. 45, No. 2.

IBM Technical Disclosure Bulletin, "Objective Image and Video Quality Assessment," Jan. 7, 2002, 6 pages.

PCT International Search Report and Written Opinion, PCT Application No. PCT/US2011/032336, Dec. 19, 2011, 11 pages.

Sheikh, H.R. et al., "Image Information and Visual Quality," IEEE Transactions on Image Processing, Feb. 2006, pp. 430-444, vol. 15, No. 2.

*Primary Examiner* — Anna Pagonakis

(74) *Attorney, Agent, or Firm* — Mintz Levin Cohn Ferris Glovsky and Popeo PC

(57) ABSTRACT

The invention provides compounds represented by the formulae: (I) and (II) where the compounds are useful in treating, for example, viral and/or parasitic infections. Also provided are pharmaceutical compositions comprising the compounds and methods of treatment using the compounds.

(I)

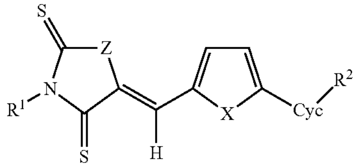

(II)

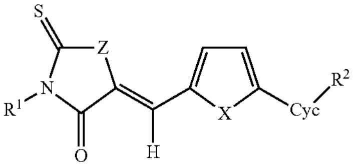

9 Claims, 5 Drawing Sheets

(56) References Cited

U.S. PATENT DOCUMENTS

| | | | | |
|---|---|---|---|---|
| 4,291,046 | A | 9/1981 | Knops et al. | |
| 5,329,379 | A | 7/1994 | Rodriguez et al. | |
| 5,426,512 | A | 6/1995 | Watson | |
| 6,054,943 | A | 4/2000 | Lawrence | |
| 6,415,057 | B1 | 7/2002 | Suzuki et al. | |
| 6,493,023 | B1 | 12/2002 | Watson | |
| 6,727,267 | B2 | 4/2004 | Jaen et al. | |
| 6,801,886 | B1 | 10/2004 | Pai et al. | |
| 7,170,933 | B2 | 1/2007 | Kouloheris et al. | |
| 8,159,960 | B2 | 4/2012 | Cooppan | |
| 2006/0034786 | A1 * | 2/2006 | Michelet et al. | 424/59 |
| 2007/0088516 | A1 | 4/2007 | Wolf et al. | |
| 2008/0064689 | A1 | 3/2008 | Carcanague et al. | |
| 2009/0052540 | A1 | 2/2009 | Gutman et al. | |
| 2010/0110199 | A1 | 5/2010 | Winkler et al. | |
| 2010/0161340 | A1 | 6/2010 | Walsh et al. | |

* cited by examiner

Alph-tocopherol blocks the antiviral activity of JL103. NDV virus encoding GFP was incubated with or without JL103 in the presence of increasing concentrations of alpha-tocopherol then used to infect Vero cells. At 24h post-infection, cells were harvested and GFP expression was measured by flow cytometry.

HIV inactivation in packed red blood cells (RBC) at an hematocrit of 80%. Packed RBC spiked with HIV (IIIB) were treated for 1h with 100 uM of the indicated compound. After treatment the serum was used to infect the reporter cells TZM-BL. At 48h after infection, luciferase expression was measured in cell lysates (RLU).

Normalized absorbtion spectra of selected compounds in DMSO. The absorbtion spectra of 100 uM solutions of selected compounds in DMSO were scanned using a Tecan Infinite® M1000 microplate reader and normalized to their absorbtion maxima.

BROAD SPECTRUM ANTIVIRAL AND ANTIPARASITIC AGENTS

RELATED APPLICATIONS

This application is the 35 USC 371 national stage entry of PCT/US2011/032336 and claims the benefit of U.S. Provisional Applications 61/323,823 filed Apr. 13, 2010 and 61/467,912 filed Mar. 25, 2011, both of which are hereby incorporated by reference in their entirety for all purposes.

STATEMENT OF GOVERNMENT SUPPORT

This invention was made with Government support of Grant Nos. AI064616 AI069317 AI 070495 and AI 082100, awarded by the National Institutes of Health. The Government has certain rights in this invention.

BACKGROUND

There are few licensed and efficacious broad-spectrum antivirals currently available. Examples include ribavirin, which functions via nebulous effects on both host and virus proteins, and alpha-interferon, which produces unwanted side effects and remains impractically expensive for widespread use (Tam et al., *Antivir Chem Chemother,* 12:261-72 (2001); Bekisz et al., *Growth Factors,* 22:243-51 (2004); de Veer et al., *J Leukoc Biol,* 69:912-20 (2001); Sen, *Annu Rev Microbiol,* 55:255-81 (2001); Hong and Cameron, *Prog Drug Res,* 59:41-69 (2002)). The prevailing paradigm in antiviral research emphasizes a "one bug-one drug" strategy; however, the rapid rise in the number of emerging viral pathogens brings into stark contrast the limited resources available to develop therapeutics on a single-pathogen basis (see e.g., Burroughs et al., "The Emergence of Zoonotic Diseases: Understanding the Impact on Animal and Human Health," *Workshop Summary from Board on Global Health, Institute of Medicine*, National Academy Press, Washington, D.C. (2002)). The expense and difficulty of developing antiviral drugs tailored to specific pathogens underscores the need to develop broad spectrum antiviral drugs against targets that are common among large classes of viruses.

Viruses can be categorized as either lipid-enveloped or non-enveloped (naked). Enveloped viruses replicate within the host-cell, recruit viral proteins to the host membrane, and then bud from and utilize the host membrane, essentially, as a vehicle to transport the viral genome to new cellular targets. Although the lipid membrane of enveloped viruses derives from the host cell, it differs from host cellular membranes in several biochemical and biophysical properties, such as biogenic reparative capacity, fluidity, lipid composition, and curvature. For example, the membranes of budding viral particles are highly curved relative to the membranes of much larger host cells. As a result, the fusion of enveloped viral particles with new host cells requires that the high curvature viral membranes undergo elastic stresses and subsequent negative curvature needed to promote fusion between the juxtaposed outer lipid monolayers of the viral particles and host cell membranes (Chemomordik et al., *J Cell Biol,* 175:201-7 (2006); McMahon and Gallop, *Nature,* 438:590-6 (2005); Chemomordik and Kozlov, Annu Rev Biochem, 72:175-207 (2003)).

The central role of virus-host cell fusion in the infectivity of enveloped viruses has motivated the development of small molecule antiviral therapeutics that insert, intercalate, or otherwise bind to viral membranes and disturb the membrane dynamics required for successful virus-host cell fusion (e.g., Chemomordik et al., *J Cell Biol,* 175:201-7 (2006); Martin and Ruysschaert, *Biochim Biophys Acta,* 1240:95-100 (1995); Langosch et al., *J Biol Chem,* 276:32016-21 (2001); Langosch et al., *Cell Mol Life Sci,* 64:850-64 (2007)). For example, the phospholipid analog lysophosphotidylcholine (LPC) is designed to prevent the entry of certain enveloped viruses, such as influenza, HIV-1 (Class I fusion) and TBEV (Class II fusion), into host cell by stabilizing the positive spontaneous curvature of viral membranes and thereby preventing conformational changes needed for viral-host cell fusion (Chemomordik et al., *J Cell Biol,* 175:201-7 (2006); Chemomordik and Kozlov, *Annu Rev Biochem,* 72:175-207 (2003); Martin and Ruysschaert, *Biochim Biophys Acta,* 1240:95-100 (1995); Razinkov et al., *J Gen Physiol,* 112:409-22 (1998); Shangguan et al., *Biochemistry,* 35:4956-65 (1996); Gunther-Ausborn et al., *J Biol Chem,* 270:29279-85 (1995)). However, LPC's viability as a drug candidate is questionable since it exerts its effect in a highly reversible manner, requires high molar concentrations (10% or higher total lipid content), and can be effectively recycled and metabolized by cells.

n-docosanol, a 22-carbon saturated alcohol, is also designed to inhibit host cell entry of a variety of enveloped viruses (Katz et al., *Proc Natl Acad Sci USA,* 88:10825-9 (1991)). However, n-docosanol appears to inhibit virus-cell fusion by perturbing the properties of the target cell rather than the virus (Katz et al., *Ann N Y Acad Sci,* 724:472-88 (1994); Marcelletti et al., *AIDS Res Hum Retroviruses,* 12:71-4 (1996); Pope et al., *Antiviral Res,* 40:85-94 (1998)), as optimal inhibition is observed when cells, but not virus, are pre-incubated for several hours with n-docosanol. In addition, poor solubility and a millimolar $IC_{50}$ has limited n-docosanol to use as a 10% v/v topical microbicide (Abreva™) for the treatment of cold sores (Katz et al., *Ann N Y Acad Sci,* 724:472-88 (1994); Marcelletti et al., *AIDS Res Hum Retroviruses,* 12:71-4 (1996); Pope et al., *Antiviral Res,* 40:85-94 (1998)).

Recently, amphipathic peptides derived from the NS5A protein of Hepatitis C have been identified as having antiviral activity related to their ability to disrupt the membrane integrity of enveloped viruses (Bobardt et al., *Proc Natl Acad Sci USA,* 105:5525-30 (2008); Cheng et al., *Proc Natl Acad Sci USA,* 105:3088-93 (2008)). Although the NS5A-derived peptides were not active against all enveloped viruses, their broad range of activity validates viral membranes as a therapeutic target for broad spectrum antiviral therapeutics.

Thus, there is a need in the art for broad-spectrum antiviral drugs capable of disrupting viral lipid membranes and thereby preventing viral infections.

*Toxoplasma gondii* is an obligate intracellular parasite in the phylum Apicomplexa that causes severe central nervous system disorders of immunocompromised (AIDS/transplant/lymphoma) individuals, birth defects in congenitally infected neonates, and ocular disease in immunocompetent persons. In addition to being an important pathogen in its own right, *Toxoplasma* serves as a model system for studying apicomplexan parasites which cause a number of diseases of medical and veterinary importance worldwide. There are over 5000 different species of apicomplexans, but the most notable of these is *Plasmodium falciparum*, the causative agent of malaria which kills 1-2 million people each year. Other Apicomplexans which cause disease in humans include the opportunistic pathogens *Cryptosporidia* spp. and *Isospora belli.* Important veterinary pathogens include *Neospora caninum* (a pathogen of dogs/cattle), *Theileria* spp (cattle), and *Eimeria* spp (poultry).

Apicomplexan parasites share a common mechanism of gliding motility that drives invasion into the host cell, a process that is essential for survival. The parasites secrete an array of molecular adhesins from a specialized secretory organelle named the micronemes onto the surface of the parasite which mediate motility and attachment to the host cell. The cytoplasmic tails of these adhesins interact with a parasite actin:myosin motor which is anchored in a membrane system underlying the plasma membrane known as the inner membrane complex. Action on the actin:myosin motor provides the driving force for motility, and also for the parasites to actively penetrate their respective host cells. In *Toxoplasma* and *Plasmodium*, the micronemal protein AMA1 also has been shown to organize the moving junction RON proteins which are secreted from another organelle called the rhoptries and this complex of proteins is critical for subsequent invasion. Current antiparasite therapies target biosynthetic pathways in the parasite and the bacterial-like apicoplast and are prone to mutations leading to resistance.

Thus, there is a need in the art for broad-spectrum antiparasitic drugs that are less susceptible to resistance through mutation.

SUMMARY

In a first embodiment, a compound is provided according to formula Ia or a pharmaceutically acceptable salt thereof, (Ia)

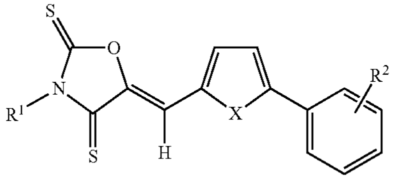

wherein $R^1$ is H, $C_1$-$C_6$ alkyl, $C_2$-$C_6$ alkenyl, $C_2$-$C_6$ alkynyl, $C_1$-$C_6$ alkoxy, $C_3$-$C_6$ aryl, $C_3$-$C_6$ heteroaryl, $C_3$-$C_6$ cycloalkyl, or $C_3$-$C_6$ heterocycloalkyl, each optionally substituted with halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$; halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$;

$R^2$ represents one or more substituents independently selected from —$OR^3$, —$SR^3$, and —$NR^4R^5$;

$R^3$, $R^4$, and $R^5$ are independently H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$; and X is O, N, S, NH, or $NR^3$.

In a second embodiment, a compound is provided according to formula IIa or a pharmaceutically acceptable salt thereof, (IIa)

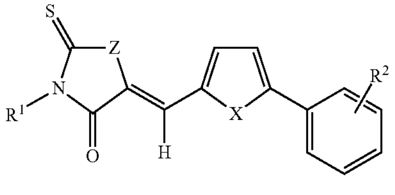

wherein $R^1$ is H, $C_1$-$C_6$ alkyl, $C_2$-$C_6$ alkenyl, $C_2$-$C_6$ alkynyl, each optionally substituted with halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$; halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$;

$R^2$ represents exactly one —$OR^3$, —$SR^3$, or —$NR^4R^5$;

$R^3$, $R^4$, and $R^5$ are independently H, $C_1$-$C_6$ alkyl, $C_2$-$C_6$ alkenyl, $C_2$-$C_6$ alkynyl, or $C_1$-$C_6$ alkoxy, halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$;

X is O, N, S, NH, or $NR^3$; and

Z is O, N, NH, or $NR^3$.

In one aspect of the first or second embodiment, $R^3$, $R^4$, and $R^5$ are independently $C_1$-$C_6$ alkyl, $C_2$-$C_6$ alkenyl, or $C_2$-$C_6$ alkynyl.

In one aspect of the first or second embodiment, $R^1$ is $C_1$-$C_6$ alkyl.

In a third embodiment, a method of treating or preventing a disease or condition caused by infection with an enveloped virus is provided, the method comprising administering to a subject a therapeutically effective amount of a compound of formula Ia or formula IIa.

In a first aspect of the third embodiment, a method of treating or preventing a disease or condition caused by infection with an enveloped virus is provided, the method comprising administering to a subject a therapeutically effective amount of a compound according to formula IIa or a pharmaceutically acceptable salt thereof, (IIa)

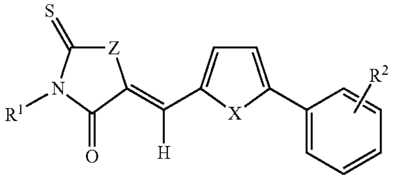

wherein $R^1$ is H, $C_1$-$C_6$ alkyl, $C_2$-$C_6$ alkenyl, or $C_2$-$C_6$ alkynyl, each optionally substituted with halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$; halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$;

$R^2$ represents one or more substituents independently selected from H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$;

$R^3$, $R^4$, and $R^5$ are independently H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$;

X is O, N, S, NH, or $NR^3$; and

Z is O, N, NH, or $NR^3$.

In a second aspect of the third embodiment, the virus is hepatitis C virus (HCV), human immunodeficiency virus (HIV), herpes simplex virus type 1 (HSV-1), herpes simplex virus type 2 (HSV-2), Ebola virus, Influenza virus, Nipah virus, Yellow Fever Virus, Dengue virus, Rift Valley Fever Virus, West Nile Virus.

In a third aspect of the third embodiment, the compound is administered as a liposomal formulation.

In a fourth embodiment, a pharmaceutical composition comprising a compound of formula Ia or formula IIa and at least one pharmaceutically acceptable excipient is provided. In a first aspect of the fourth embodiment, the composition is suitable as a topical formulation. In a second aspect of the fourth embodiment, the composition is in the form of a patch, an ointment, a cream, a lotion, a drop, a spray, or an aerosol. In a third aspect of the fourth embodiment, the composition is in the form of a liposomal formulation.

In a fifth embodiment, a method of treating or preventing a disease or condition caused by infection with a parasite is provided, the method comprising administering to a subject a therapeutically effective amount of the compound for formula Ia or formula IIa.

In a sixth embodiment, a method of treating or preventing a disease or condition caused by infection with a parasite is provided, the method comprising administering to a subject a therapeutically effective amount of a compound according to formula IIa or a pharmaceutically acceptable salt thereof, (IIa)

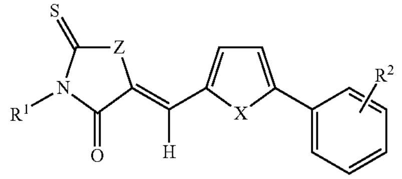

wherein $R^1$ is H, $C_1$-$C_6$ alkyl, $C_2$-$C_6$ alkenyl, $C_2$-$C_6$ alkynyl, $C_1$-$C_6$ alkoxy, $C_3$-$C_6$ aryl, $C_3$-$C_6$ heteroaryl, $C_3$-$C_6$ cycloalkyl, or $C_3$-$C_6$ heterocycloalkyl, each optionally substituted with halo, —$NO_2$, —$CF_3$, —CN, —$OR^3$, —$SR^3$, —$C(O)R^3$, —$NHC(O)R^3$, —$C(O)OR^3$, —$OC(O)R^3$, —$NR^4R^5$, —$C(O)NR^4R^5$, —$NHR^3C(O)NR^4R^5$, or —$SO_2NR^4R^5$; halo, —$NO_2$, —$CF_3$, —CN, —$OR^3$, —$SR^3$, —$C(O)R^3$, —$NHC(O)R^3$, —$C(O)OR^3$, —$OC(O)R^3$, —$NR^4R^5$, —$C(O)NR^4R^5$, —$NHR^3C(O)NR^4R^5$, or —$SO_2NR^4R^5$;

$R^2$ represents one or more substituents independently selected from —$OR^3$, —$SR^3$, and —$NR^4R^5$;

$R^3$, $R^4$, and $R^5$ are independently H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —$C(O)R^3$, —$NHC(O)R^3$, —$C(O)OR^3$, —$OC(O)R^3$, —$NR^4R^5$, —$C(O)NR^4R^5$, —$NHR^3C(O)NR^4R^5$, or —$SO_2NR^4R^5$;

X is O, N, S, NH, or $NR^3$; and

Z is O, N, NH, or $NR^3$.

DETAILED DESCRIPTION

Figure 1:
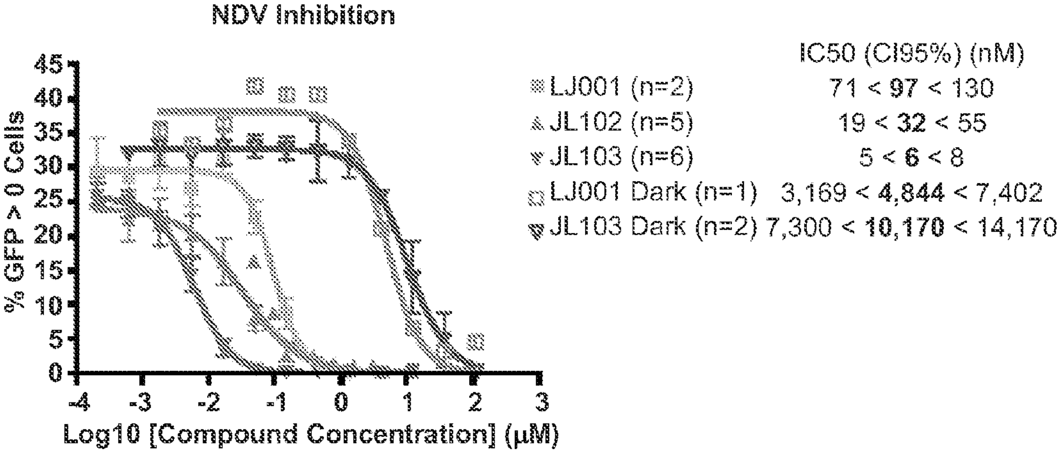
FIG. 1 shows compounds-mediated inhibition of NDV infection. Virus and compounds, at the indicated concentration, were incubated under light for 10 minutes and used to infect Vero cells. 24 hours later, GFP expression in cells was analyzed by flow cytometry. n=number of independent experiments pooled. Inhibitory concentration 50% (IC50 and 95% confidence interval (CI95%) are indicated.

Provided herein are a series of oxazolidine-2,4-dithiones having broad-spectrum antiviral activity. These compounds are novel photosensitizers that act as broad-spectrum, virucidal antivirals that prevent infection of a variety of viruses, especially lipid bilayer encapsulated (enveloped) viruses. Without being limited to a particular theory, it is believed that the compounds are capable of binding and/or inserting into the outer membranes of enveloped viruses and disrupting the membrane structure and/or dynamics in a manner that inhibits viral attachment, fusion, and/or entry into host cells. Moreover, the membrane disrupting activity of the compounds is preferably selective for viral membranes relative to non-viral biological membranes, including but not limited to, cell plasma membranes, organelle membranes, biological barriers, and other non-viral lipid bilayers. Thus, compounds provided herein are substantially non-toxic and have a wide therapeutic index for antiviral activity in vivo without significant toxicity or side effects. Because membranes are common to all enveloped viruses, compounds provided herein have broad ranging antiviral activity against enveloped viruses, including but not limited to, filoviruses, poxviruses, arenaviruses, bunyaviruses, paramyxoviruses, flaviviruses, influenza A, and HIV-1.

In some aspects, antiviral compounds of formula I, and pharmaceutically acceptable salts, prodrugs, and derivatives thereof, are provided herein (I)

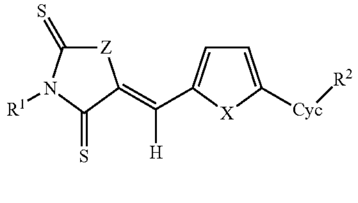

wherein $R^1$ is H, $C_1$-$C_6$ alkyl, $C_2$-$C_6$ alkenyl, $C_2$-$C_6$ alkynyl, $C_1$-$C_6$ alkoxy, $C_3$-$C_6$ aryl, $C_3$-$C_6$ heteroaryl, $C_3$-$C_6$ cycloalkyl, or $C_3$-$C_6$ heterocycloalkyl, each optionally substituted with halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —NH$R^3$C(O)$NR^4R^5$, or —$SO_2NR^4R^5$; halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —NH$R^3$C(O)$NR^4R^5$, or —$SO_2NR^4R^5$;

$R^2$ represents one or more substituents to the ring to which it is attached, independently selected from H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —NH$R^3$C(O)$NR^4R^5$, —$SO_2NR^4R^5$, aryl, or heteroaryl;

$R^3$, $R^4$, and $R^5$ are independently H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —NH$R^3$C(O)$NR^4R^5$, or —$SO_2NR^4R^5$;

Cyc is aryl or heteroaryl;

X is O, N, S, NH, or $NR^3$; and

Z is O, N, NH, or $NR^3$.

In some preferred aspects of formula I, Z is O or NH.

In some aspects, antiviral compounds of formula Ia, and pharmaceutically acceptable salts, prodrugs, and derivatives thereof, are provided herein (Ia)

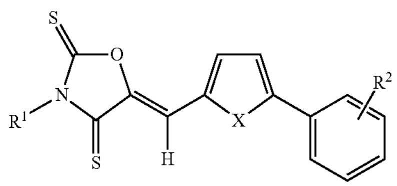

wherein $R^1$ is H, $C_1$-$C_6$ alkyl, $C_2$-$C_6$ alkenyl, $C_2$-$C_6$ alkynyl, $C_1$-$C_6$ alkoxy, $C_3$-$C_6$ aryl, $C_3$-$C_6$ heteroaryl, $C_3$-$C_6$ cycloalkyl, or $C_3$-$C_6$ heterocycloalkyl, each optionally substituted with halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —NH$R^3$C(O)$NR^4R^5$, or —$SO_2NR^4R^5$; halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —NH$R^3$C(O)$NR^4R^5$, or —$SO_2NR^4R^5$;

$R^2$ represents one or more substituents to the ring to which it is attached, independently selected from H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —NH$R^3$C(O)$NR^4R^5$, or —$SO_2NR^4R^5$;

$R^3$, $R^4$, and $R^5$ are independently H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —NH$R^3$C(O)$NR^4R^5$, or —$SO_2NR^4R^5$; and X is O, N, S, NH, or $NR^3$.

In some preferred aspects of formulas I and Ia, X is O or N—$CH_3$.

In some preferred embodiments of formula I and Ia, $R^1$ is other than H, such as $C_1$-$C_6$ alkyl, $C_2$-$C_6$ alkenyl, or $C_2$-$C_6$ alkynyl, most preferably methyl, ethyl, propyl or propenyl.

In some preferred embodiments of formulas I and Ia, each $R^2$ is independently —$OR^3$, —$SR^3$, or —$NR^4R^5$. In other preferred embodiments of formula Ia, each $R^2$ is, independently, —O—$C_1$-$C_6$ alkyl, —O—$C_2$-$C_6$ alkenyl, —O—$C_2$-$C_6$ alkynyl, —S—$C_1$-$C_6$ alkyl, —S—$C_2$-$C_6$ alkenyl, —S—$C_2$-$C_6$ alkynyl or —N($C_1$-$C_6$ alkyl)($C_1$-$C_6$ alkyl). In yet other preferred embodiments, each $R^2$ is independently preferably —OMe, —OEt, —OPr, —SMe, —SEt, —SPr, —N(Me)(Me), —N(Et)(Et) or —N(Pr)(Pr), and most preferably —OMe or —N(Me)(Me). In some preferred embodiments of formulas I and Ia, more than one $R^2$ is present. In some such embodiments, all $R^2$ substituents are identical. In other aspects, exactly one $R^2$ is present.

In some preferred embodiments of formula Ia:

$R^1$ is $C_1$-$C_6$ alkyl, $C_2$-$C_6$ alkenyl, or $C_2$-$C_6$ alkynyl;

X is O or S; and one to three $R^2$ substituents are present, each independently selected from —O—$C_1$-$C_6$ alkyl, —O—$C_2$-$C_6$ alkenyl, —O—$C_2$-$C_6$ alkynyl, —S—$C_1$-$C_6$ alkyl, —S—$C_2$-$C_6$ alkenyl, —S—$C_2$-$C_6$ alkynyl, and —N($C_1$-$C_6$ alkyl)($C_1$-$C_6$ alkyl).

In some preferred embodiments of formula Ia:

$R^1$ is $C_1$-$C_3$ alkyl;

X is O or S; and one to three $R^2$ substituents are present, each independently selected from —O—$C_1$-$C_3$ alkyl, —S—$C_1$-$C_3$ alkyl, and —N($C_1$-$C_3$ alkyl)($C_1$-$C_3$ alkyl).

In yet other preferred embodiments of formula Ia, $R^1$ is $C_1$-$C_3$ alkyl, X is O, Z is O, and two $R^2$ substituents are present, each independently —O—$C_1$-$C_3$ alkyl.

Also provided herein are antiviral compounds of formula II, and pharmaceutically acceptable salts, prodrugs, and derivatives thereof, are provided herein (II)

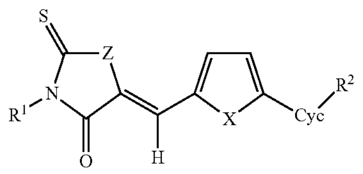

wherein $R^1$ is H, $C_1$-$C_6$ alkyl, $C_2$-$C_6$ alkenyl, $C_2$-$C_6$ alkynyl, $C_1$-$C_6$ alkoxy, $C_3$-$C_6$ aryl, $C_3$-$C_6$ heteroaryl, $C_3$-$C_6$ cycloalkyl, or $C_3$-$C_6$ heterocycloalkyl, each optionally substituted with halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —NH$R^3$C(O)$NR^4R^5$, or —$SO_2NR^4R^5$; halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —NH$R^3$C(O)$NR^4R^5$, or —$SO_2NR^4R^5$;

$R^2$ represents one or more substituents to the ring to which it is attached, independently selected from H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$SR^3$, —C(O)$R^3$, —NHC(O)$R^3$, —C(O)O$R^3$, —OC(O)$R^3$, —$NR^4R^5$, —C(O)$NR^4R^5$, —NH$R^3$C(O)$NR^4R^5$, —$SO_2NR^4R^5$, aryl, or heteroaryl;

$R^3$, $R^4$, and $R^5$ are independently H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —NH$R^3$C(O)$NR^4R^5$, or —$SO_2NR^4R^5$;

Cyc is aryl or heteroaryl;

X is O, N, S, NH, or $NR^3$; and

Z is O, N, NH, or $NR^3$.

Also provided herein are antiviral compounds of formula IIa, and pharmaceutically acceptable salts, prodrugs, and derivatives thereof, are provided herein (IIa)

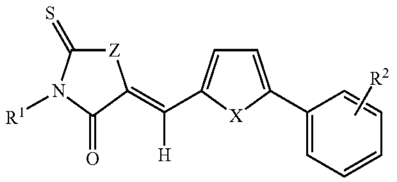

wherein $R^1$ is H, $C_1$-$C_6$ alkyl, $C_2$-$C_6$ alkenyl, $C_2$-$C_6$ alkynyl, $C_1$-$C_6$ alkoxy, $C_3$-$C_6$ aryl, $C_3$-$C_6$ heteroaryl, $C_3$-$C_6$ cycloalkyl, or $C_3$-$C_6$ heterocycloalkyl, each optionally substituted with halo, —$NO_2$, —$CF_3$, —CN, —$OR^3$, —$SR^3$, —$C(O)R^3$, —$NHC(O)R^3$, —$C(O)OR^3$, —$OC(O)R^3$, —$NR^4R^5$, —$C(O)NR^4R^5$, —$NHR^3C(O)NR^4R^5$, or —$SO_2NR^4R^5$; halo, —$NO_2$, —$CF_3$, —CN, —$OR^3$, —$SR^3$, —$C(O)R^3$, —$NHC(O)R^3$, —$C(O)OR^3$, —$OC(O)R^3$, —$NR^4R^5$, —$C(O)NR^4R^5$, —$NHR^3C(O)NR^4R^5$, or —$SO_2NR^4R^5$;

$R^2$ represents one or more substituents to the ring to which it is attached, independently selected from H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —$C(O)R^3$, —$NHC(O)R^3$, —$C(O)OR^3$, —$OC(O)R^3$, —$NR^4R^5$, —$C(O)NR^4R^5$, —$NHR^3C(O)NR^4R^5$, or —$SO_2NR^4R^5$;

$R^3$, $R^4$, and $R^5$ are independently H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —$C(O)R^3$, —$NHC(O)R^3$, —$C(O)OR^3$, —$OC(O)R^3$, —$NR^4R^5$, —$C(O)NR^4R^5$, —$NHR^3C(O)NR^4R^5$, or —$SO_2NR^4R^5$;

X is O, N, S, NH, or $NR^3$; and

Z is O, N, NH, or $NR^3$.

In some preferred aspects of formula IIa, X is O.

In some preferred aspects of formulas II and IIa, Z is O. In other preferred aspects of formulas II and IIa, Z is NH.

In some preferred embodiments of formulas II and IIa, $R^1$ is other than H, such as methyl, ethyl or propyl, preferably ethyl. In other embodiments, $R^1$ is H, $C_1$-$C_6$ alkyl, $C_2$-$C_6$ alkenyl, or $C_2$-$C_6$ alkynyl.

In some preferred embodiments of formulas II and IIa, each $R^2$ is H. In other preferred embodiments, of formula IIa, each $R^2$ is independently —$OR^3$, —$SR^3$, or —$NR^4R^5$. In some such embodiments, all $R^2$ substituents are identical.

In some aspects, the antiviral compounds of formulas I and Ia are:

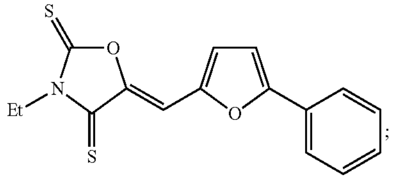

(i.e., LJ-046 = JL102)

-continued

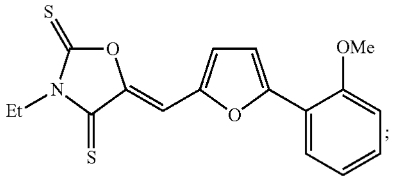

(i.e., LJ-052 = JL103)

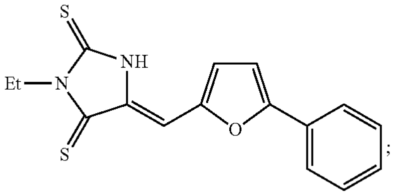

(i.e., JL105)

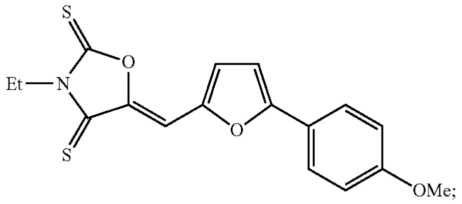

(i.e., JL108)

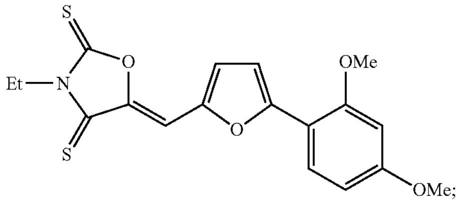

(i.e., JL109)

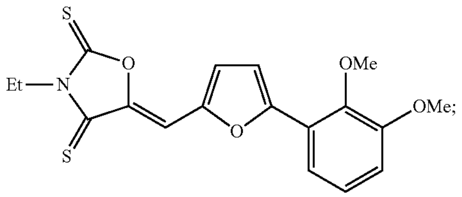

(i.e., JL110)

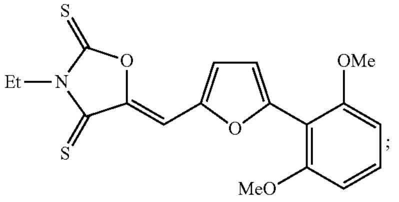

(i.e., JL111)

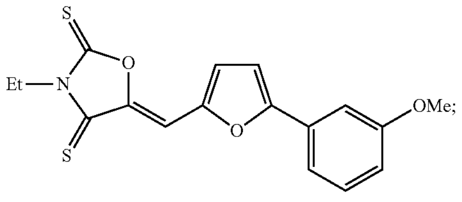

(i.e., JL117)

-continued

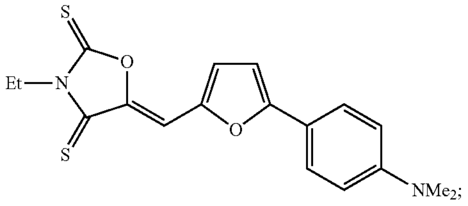

(i.e., JL118)

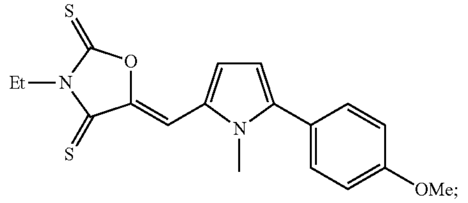

(i.e., JL119)

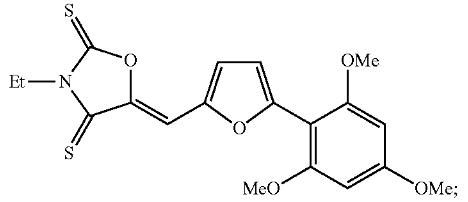

(i.e., JL122)

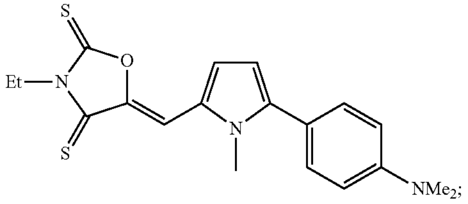

(i.e., JL123)

(Z)-3-ethyl-5-((5-phenylfuran-2-yl)methylene)oxazolidine-2,4-dithione (i.e., JL102); or (Z)-3-ethyl-5-((5-(2-methoxyphenyl)furan-2-yl)methylene)oxazolidine-2,4-dithione (i.e., JL103)

In further aspects, the antiviral compound of formulas IIa is:

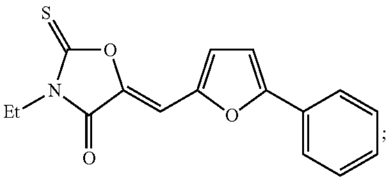

(i.e., LJ-045 = JL101)

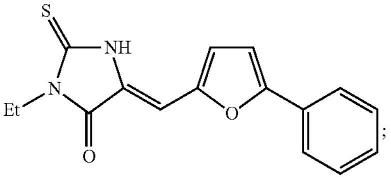

(i.e., LJ-048 = JL104)

-continued

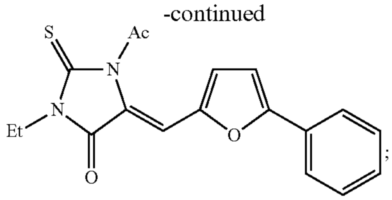

; or (i.e., LJ-049 = JL105a)

(Z)-3-ethyl-5-((5-phenylfuran-2-yl)methylene)-2-thioxooxazolidine-4-one (i.e., JL101)

In some aspects, antiparasitic compounds of formula III, and pharmaceutically acceptable salts, prodrugs, and derivatives thereof, are provided herein (III)

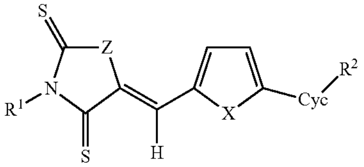

wherein $R^1$ is H, $C_1$-$C_6$ alkyl, $C_2$-$C_6$ alkenyl, $C_2$-$C_6$ alkynyl, $C_1$-$C_6$ alkoxy, $C_3$-$C_6$ aryl, $C_3$-$C_6$ heteroaryl, $C_3$-$C_6$ cycloalkyl, or $C_3$-$C_6$ heterocycloalkyl, each optionally substituted with halo, —$NO_2$, —$CF_3$, —CN, —$OR^3$, —$SR^3$, —$C(O)R^3$, —$NHC(O)R^3$, —$C(O)OR^3$, —$OC(O)R^3$, —$NR^4R^5$, —$C(O)NR^4R^5$, —$NHR^3C(O)NR^4R^5$, or —$SO_2NR^4R^5$; halo, —$NO_2$, —$CF_3$, —CN, —$OR^3$, —$SR^3$, —$C(O)R^3$, —$NHC(O)R^3$, —$C(O)OR^3$, —$OC(O)R^3$, —$NR^4R^5$, —$C(O)NR^4R^5$, —$NHR^3C(O)NR^4R^5$, or —$SO_2NR^4R^5$;

$R^2$ represents one or more substituents to the ring to which it is attached, independently selected from H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —$C(O)R^3$, —$NHC(O)R^3$, —$C(O)OR^3$, —$OC(O)R^3$, —$NR^4R^5$, —$C(O)NR^4R^5$, —$NHR^3C(O)NR^4R^5$, —$SO_2NR^4R^5$, aryl, or heteroaryl;

$R^3$, $R^4$, and $R^5$ are independently H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —$C(O)R^3$, —$NHC(O)R^3$, —$C(O)OR^3$, —$OC(O)R^3$, —$NR^4R^5$, —$C(O)NR^4R^5$, —$NHR^3C(O)NR^4R^5$, or —$SO_2NR^4R^5$;

Cyc is aryl or heteroaryl;

X is O, N, S, NH, or $NR^3$; and

Z is O, N, NH, or $NR^3$.

In some preferred aspects of formula III, Z is O or NH.

In some aspects, antiparasitic compounds of formula IIIa, and pharmaceutically acceptable salts, prodrugs, and derivatives thereof, are provided herein (IIIa)

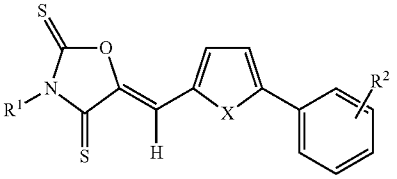

wherein $R^1$ is H, $C_1$-$C_6$ alkyl, $C_2$-$C_6$ alkenyl, $C_2$-$C_6$ alkynyl, $C_1$-$C_6$ alkoxy, $C_3$-$C_6$ aryl, $C_3$-$C_6$ heteroaryl, $C_3$-$C_6$ cycloalkyl, or $C_3$-$C_6$ heterocycloalkyl, each optionally substituted with halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$; halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$;

$R^2$ represents one or more substituents to the ring to which it is attached, independently selected from H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$;

$R^3$, $R^4$, and $R^5$ are independently H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$; and X is O, N, S, NH, or $NR^3$.

In some preferred aspects of formula IIIa, X is O or N—$CH_3$.

In some preferred embodiments of formulas III and IIIa, $R^1$ is other than H, such as $C_1$-$C_6$ alkyl, $C_2$-$C_6$ alkenyl, or $C_2$-$C_6$ alkynyl, most preferably methyl, ethyl, propyl or propenyl. In other embodiments, $R^1$ is H, $C_1$-$C_6$ alkyl, $C_2$-$C_6$ alkenyl, or $C_2$-$C_6$ alkynyl.

In some preferred embodiments of formulas III and IIIa, each $R^2$ is independently —$OR^3$, —$SR^3$, or —$NR^4R^5$. In other preferred embodiments of formulas IIIa, each $R^2$ is, independently, —O—$C_1$-$C_6$ alkyl, —O—$C_2$-$C_6$ alkenyl, —O—$C_2$-$C_6$ alkynyl, —S—$C_1$-$C_6$ alkyl, S—$C_2$-$C_6$ alkenyl, —S—$C_2$-$C_6$ alkynyl or —N($C_1$-$C_6$ alkyl)($C_1$-$C_6$ alkyl). In other preferred embodiments, each $R^2$ is independently preferably —OMe, —OEt, —OPr, —SMe, —SEt, —SPr, —N(Me)(Me), —N(Et)(Et) or —N(Pr)(Pr), and most preferably —OMe or —N(Me)(Me). In some preferred embodiments of formulas III and IIIa, more than one $R^2$ is present. In some such embodiments, all $R^2$ substituents are identical. In other aspects, exactly one $R^2$ is present.

In some preferred embodiments of formula IIIa:

$R^1$ is $C_1$-$C_6$ alkyl, $C_2$-$C_6$ alkenyl, or $C_2$-$C_6$ alkynyl;

X is O or S; and one to three $R^2$ substituents are present, each independently selected from —O—$C_1$-$C_6$ alkyl, —O—$C_2$-$C_6$ alkenyl, —O—$C_2$-$C_6$ alkynyl, —S—$C_1$-$C_6$ alkyl, —S—$C_2$-$C_6$ alkenyl, —S—$C_2$-$C_6$ alkynyl, and —N($C_1$-$C_6$ alkyl)($C_1$-$C_6$ alkyl).

In some preferred embodiments of formula IIIa:

$R^1$ is $C_1$-$C_3$ alkyl;

X is O or S; and one to three $R^2$ substituents are present, each independently selected from —O—$C_1$-$C_3$ alkyl, —S—$C_1$-$C_3$ alkyl, and —N($C_1$-$C_3$ alkyl)($C_1$-$C_3$ alkyl).

In yet other preferred embodiments of formula IIIa, $R^1$ is $C_1$-$C_3$ alkyl, X is O; and two $R^2$ substituents are present, each independently —O—$C_1$-$C_3$ alkyl.

Also provided herein are antiparasitic compounds of formula IV, and pharmaceutically acceptable salts, prodrugs, and derivatives thereof, are provided herein (IV)

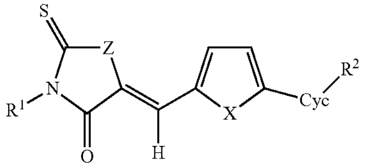

wherein $R^1$ is H, $C_1$-$C_6$ alkyl, $C_2$-$C_6$ alkenyl, $C_2$-$C_6$ alkynyl, $C_1$-$C_6$ alkoxy, $C_3$-$C_6$ aryl, $C_3$-$C_6$ heteroaryl, $C_3$-$C_6$ cycloalkyl, or $C_3$-$C_6$ heterocycloalkyl, each optionally substituted with halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$; halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$;

$R^2$ represents one or more substituents to the ring to which it is attached, independently selected from H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, —$SO_2NR^4R^5$, aryl, or heteroaryl;

$R^3$, $R^4$, and $R^5$ are independently H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$;

Cyc is aryl or heteroaryl;

X is O, N, S, NH, or $NR^3$; and

Z is O, N, NH, or $NR^3$.

Also provided herein are antiparasitic compounds of formula IVa, and pharmaceutically acceptable salts, prodrugs, and derivatives thereof, are provided herein (IVa)

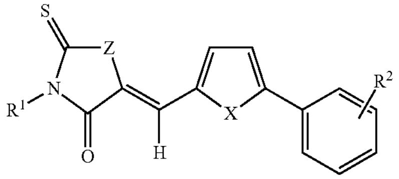

wherein $R^1$ is H, $C_1$-$C_6$ alkyl, $C_2$-$C_6$ alkenyl, $C_2$-$C_6$ alkynyl, $C_1$-$C_6$ alkoxy, $C_3$-$C_6$ aryl, $C_3$-$C_6$ heteroaryl, $C_3$-$C_6$ cycloalkyl, or $C_3$-$C_6$ heterocycloalkyl, each optionally substituted with halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$; halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$;

$R^2$ represents one or more substituents to the ring to which it is attached, independently selected from H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —C(O)$R^3$, —NHC(O)$R^3$, —C(O)O$R^3$, —OC(O)$R^3$, —$NR^4R^5$, —C(O)$NR^4R^5$, —$NHR^3$C(O)$NR^4R^5$, or —$SO_2NR^4R^5$;

$R^3$, $R^4$, and $R^5$ are independently H, $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^3$, —$SR^3$, —$C(O)R^3$, —$NHC(O)R^3$, —$C(O)OR^3$, —$OC(O)R^3$, —$NR^4R^5$, —$C(O)NR^4R^5$, —$NHR^3C(O)NR^4R^5$, or —$SO_2NR^4R^5$;

X is O, N, S, NH, or $NR^3$; and

Z is O, N, NH, or $NR^3$.

In some preferred aspects of formula IVa, X is O.

In some preferred aspects of formula IVa, Z is O. In other preferred aspects of formula IVa, Z is NH.

In some preferred embodiments of formula IVa, $R^1$ is other than H, such as $C_1$-$C_6$ alkyl, $C_2$-$C_6$ alkenyl, $C_2$-$C_6$ alkynyl, in particular methyl, ethyl or propyl, preferably ethyl. In other embodiments, $R^1$ is H, $C_1$-$C_6$ alkyl, $C_2$-$C_6$ alkenyl, or $C_2$-$C_6$ alkynyl.

In some preferred embodiments of formula IVa, each $R^2$ is H. In other preferred embodiments, of formula IVa, each $R^2$ is independently —$OR^3$, —$SR^3$, or —$NR^4R^5$. In some such embodiments, all $R^2$ substituents are identical.

In some aspects, the antiparasitic compounds of formulas III and IIIa are:

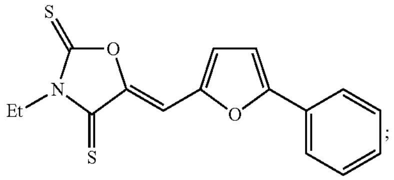

(i.e., LJ-046 = JL102)

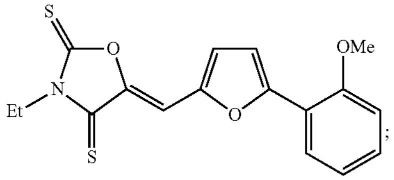

(i.e., LJ-052 = JL103)

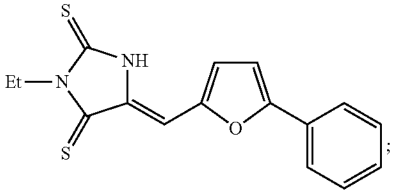

(i.e., JL105)

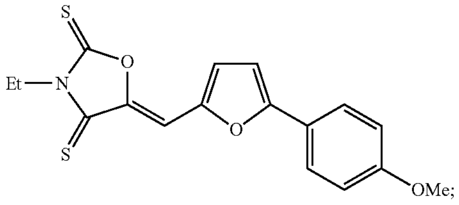

(i.e., JL108)

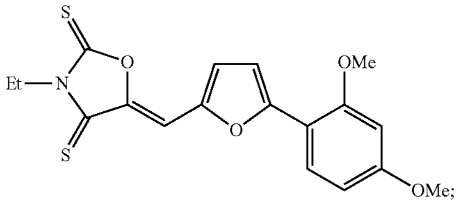

(i.e., JL109)

-continued

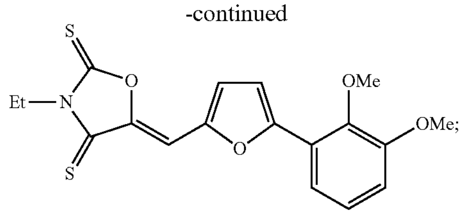

(i.e., JL110)

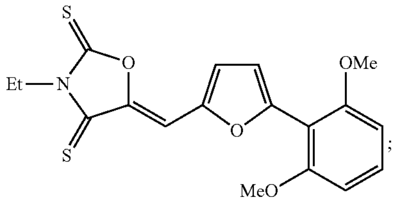

(i.e., JL111)

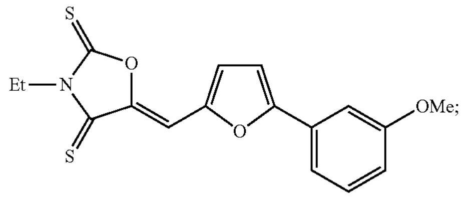

(i.e., JL117)

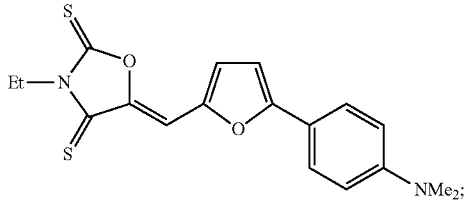

(i.e., JL118)

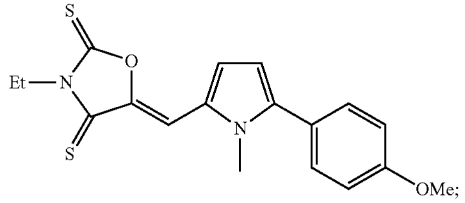

(i.e., JL119)

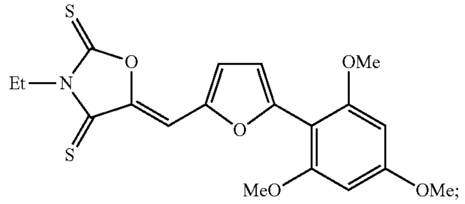

(i.e, JL122)

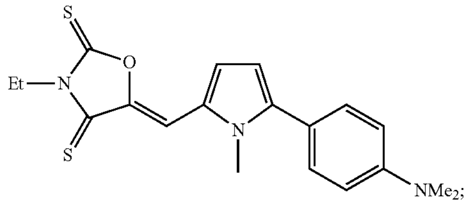

(i.e., JL123)

(Z)-3-ethyl-5-((5-phenylfuran-2-yl)methylene)oxazolidine-2,4-dithione (i.e., JL102); or (Z)-3-ethyl-5-((5-(2-methoxyphenyl)furan-2-yl)methylene)oxazolidine-2,4-dithione (i.e., JL103)

In further aspects, the antiparasitic compound of formulas IVa is:

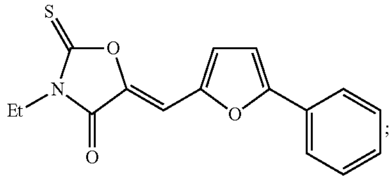
;

(i.e., LJ-045 = JL101)

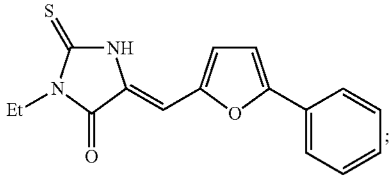
;

(i.e., LJ-048 = JL104)

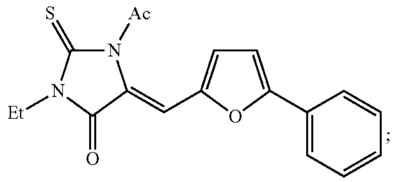
; or (i.e., LJ-049 = JL105a)

(Z)-3-ethyl-5-((5-phenylfuran-2-yl)methylene)-2-thioxooxazolidine-4-one (i.e., JL101)

In some aspects, the following antiviral compounds, and pharmaceutically acceptable salts, prodrugs, and derivatives thereof, are provided herein:

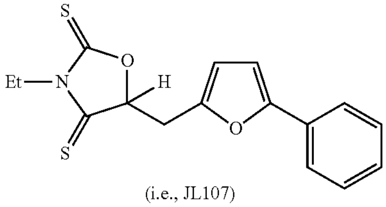
;

(i.e., JL107)

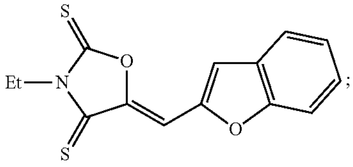
; and (i.e., JL113)

-continued

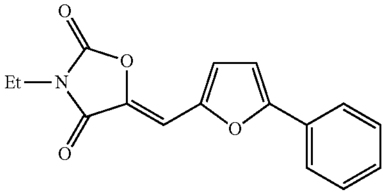
.

(i.e., JL121)

In some aspects, the following antiparasitic compounds, and pharmaceutically acceptable salts, prodrugs, and derivatives thereof, are provided herein:

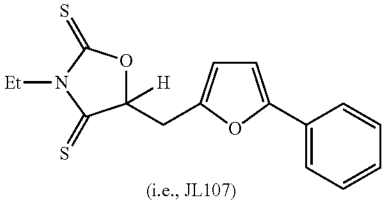
;

(i.e., JL107)

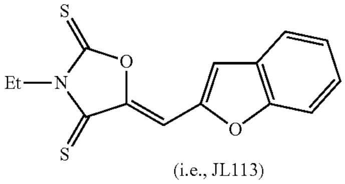
; and (i.e., JL113)

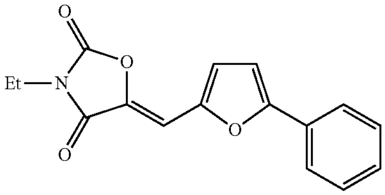
.

(i.e., JL121)

Chemical moieties referred to as univalent chemical moieties (e.g., alkyl, aryl, etc.) also encompass structurally permissible multivalent moieties, as understood by those skilled in the art. For example, while an "alkyl" moiety generally refers to a monovalent radical (e.g., $CH_3CH_2$—), in appropriate circumstances an "alkyl" moiety can also refer to a divalent radical (e.g., —$CH_2CH_2$—, which is equivalent to an "alkylene" group). Similarly, under circumstances where a divalent moiety is required, those skilled in the art will understand that the term "aryl" refers to the corresponding divalent arylene group.

All atoms are understood to have their normal number of valences for bond formation (e.g., 4 for carbon, 3 for N, 2 for O, and 2, 4, or 6 for S, depending on the atom's oxidation state). On occasion a moiety can be defined, for example, as $(A)_aB$, wherein a is 0 or 1. In such instances, when a is 0 the moiety is B and when a is 1 the moiety is AB.

Where a substituent can vary in the number of atoms or groups of the same kind (e.g., alkyl groups can be $C_1$, $C_2$, $C_3$, etc.), the number of repeated atoms or groups can be represented by a range (e.g., $C_1$-$C_6$ alkyl) which includes each and every number in the range and any and all sub ranges. For example, $C_1$-$C_3$ alkyl includes $C_1$, $C_2$, $C_3$, $C_{1-2}$, $C_{1-3}$, and $C_{2-3}$ alkyl.

The terms "alkyl," "alkenyl," and "alkynyl," refer to straight and branched chain aliphatic groups having from 1 to 30 carbon atoms, or preferably from 1 to 15 carbon atoms, or more preferably from 1 to 6 carbon atoms, each optionally substituted with one, two or three substituents depending on valency. Examples of such groups include, without limitation, methyl, ethyl, propyl, isopropyl, butyl, tert-butyl, isobutyl, pentyl, hexyl, vinyl, allyl, isobutenyl, ethynyl, and propynyl.

The term "cycloalkyl" includes saturated and partially unsaturated cyclic hydrocarbon groups having from 3 to 12, or preferably from 3 to 8, or more preferably from 3 to 6 carbon atoms, each optionally substituted with one or more substituents. Examples of cycloalkyl groups include, without limitation, cyclopropyl, cyclobutyl, cyclopentyl, cyclopentenyl, cyclohexyl, cyclohexenyl, cycloheptyl, and cyclooctyl.

An "aryl" group is an optionally substituted $C_6$-$C_{14}$ moiety comprising one to three aromatic rings. In some aspects, the aryl group is a $C_6$-$C_{10}$ aryl group, or more preferably a $C_5$-$C_6$ aryl group. Examples of aryl groups include, without limitation, phenyl, naphthyl, anthracenyl, and fluorenyl.

A "heterocyclic" or "heterocyclyl" substituent is a non-aromatic mono-, bi-, or tricyclic structure having from about 3 to about 14 atoms, including one or more heteroatoms selected from N, O, and S. One ring of a bicyclic heterocycle or two rings of a tricyclic heterocycle can be aromatic (e.g., as in indan and 9,10-dihydro anthracene). Heterocyclic groups can be optionally substituted on one or more carbon, oxygen, nitrogen and/or sulfur atoms. Examples of heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino.

A "heteroaryl" group is an aromatic ring or ring system having about 5 to 14 ring atoms, or more preferably 5, 6, 9, or 10 ring atoms, including one or more heteroatoms selected from the group consisting of N, O, and S; and 6, 10, or 14 pi electrons shared in a cyclic array. Examples of heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

A "substituted" moiety is a moiety in which one or more hydrogen atoms have been independently replaced with another chemical substituent. As a non limiting example, substituted phenyl groups include 2-fluorophenyl, 3,4-dichlorophenyl, 3-chloro-4-fluorophenyl, and 2-fluoro-3-propylphenyl. In some instances, a methylene group ($—CH_2—$) is substituted with oxygen to form a carbonyl group ($—CO$).

An "optionally substituted" group can be substituted with from one to four, or preferably from one to three, or more preferably one or two non-hydrogen substituents. Examples of suitable substituents include, without limitation, alkyl, alkenyl, alkynyl, cycloalkyl, heterocycloalkyl, aryl, heteroaryl, aroyl, halo, hydroxy, oxo, nitro, alkoxy, amino, imino, azido, mercapto, acyl, carbamoyl, carboxy, carboxamido, amidino, guanidino, sulfonyl, sulfinyl, sulfonamido, formyl, cyano, and ureido groups.

The term "halogen" or "halo" refers to chlorine, bromine, fluorine, or iodine.

The term "acyl" refers to an alkylcarbonyl or arylcarbonyl substituent.

The term "acylamino" refers to an amide substituent attached to the structure at the nitrogen atom. Acylamino groups can be optionally substituted.

The term "carbamoyl" refers to an amide substituent attached to the structure at the carbonyl carbon atom. Carbamoyl groups can be optionally substituted.

The term "sulfonamido" refers to a sulfonamide substituent attached to the structure by either the sulfur or the nitrogen atom.

Unless otherwise specified, compounds provided herein include all of their various stereochemical forms, including but not limited to, enantiomers, diastereomers, rotamers, and the like. Also, moieties disclosed herein which exist in multiple tautomeric forms include all such forms encompassed by a given tautomeric structure.

Particular geometric isomers (e.g., E or Z isomers) disclosed herein include the E or Z isomer substantially free from the other isomer as well as mixtures of E and Z isomers in varying ratios. For example, in some preferred aspects, compounds provided herein comprise the (Z)-isomer substantially free from the (E)-isomer.

Certain E and Z geometric isomers can be interconverted by photolysis, photo irradiation or exposure to free radicals or certain solvents (see e.g., Ishida et al., *Tetrahedron Lett* 30:959 (1989)). For example, exposure of some (E) compounds to DMSO facilitates their conversion to the Z form.

Compounds provided herein can form useful salts with inorganic and organic acids, such as hydrochloric, sulfuric, acetic, lactic, or the like, and with inorganic or organic bases such as sodium or potassium hydroxide, piperidine, morpholine, ammonium hydroxide, or the like. Pharmaceutically acceptable salts of compounds provided herein can be prepared using procedures familiar to those skilled in the art.

Also provided herein are pharmaceutical compositions comprising an antiviral compound described herein and at least one pharmaceutically acceptable excipient.

The term "pharmaceutically acceptable excipient" includes any and all salts, buffering agents, preservatives, solvents, diluents, carriers, liquid vehicles, dispersion or suspension aids, surface active agents, isotonic agents, thickening or emulsifying agents, preservatives, solid binders, lubricants and the like which are compatible with the antiviral compounds provided herein and suitable for the particular dosage form desired. Various carriers, formulations, and techniques are described, e.g., in *Remington's Pharmaceutical Sciences*, E. W. Martin (Mack Publishing Co., Easton, Pa.).

Pharmaceutical compositions provided herein are formulated to be compatible with their intended route of administration. Exemplary routes of administration include, e.g., parenteral, intravenous, intramuscular, intradermal, subcutaneous, oral (e.g., inhalation), transdermal (topical), transmucosal, genital, vaginal, cervicovaginal and rectal administration.

Solutions or suspensions used for parenteral, intradermal, or subcutaneous application can include, e.g., a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

In some aspects, compounds and compositions provided herein are administered topically, e.g., by transmucosal or transdermal means. Suitable formulations for topical administration, including, e.g., vaginal or rectal administration, include solutions, suspensions, gels, lotions and creams as well as discrete units such as suppositories and microencapsulated suspensions. For transmucosal or transdermal administration, penetrants appropriate to the barrier to be permeated can be used. Such penetrants are generally known in the art, and include, for example, detergents, bile salts, and filsidic acid derivatives for transmucosal administration. Transmucosal administration can be accomplished through the use of nasal sprays, suppositories or transdermal formulations comprising active compounds formulated with ointments, salves, gels, creams, or the like.

In further aspects, compositions provided herein can be formulated as tablets, capsules or elixirs for oral administration or as sterile solutions or suspensions for injectable administration.

In some aspects, a compounds described herein is formulated as a sustained release composition which provides for slow, sustained release of the compound by a desired mode of administration. Such formulations can take the form of a sustained release gel, cream, suppository, capsule, or the like. In some aspects, active compounds are formulated within a system of carriers and excipients that protect the compound against rapid elimination from the body. Examples of such sustained release systems include: (a) erosional systems in which the active compound is contained within a matrix, and (b) diffusional systems in which the active component permeates at a controlled rate through a biocompatible polymer, such as ethylene vinyl acetate, polyanhydrides, polyglycolic acid, collagen, polyorthoesters, or polylactic acid. Methods for preparation of such formulations are known to those skilled in the art.

Pharmaceutical compositions provided herein can be utilized in conjunction with a delivery device, such as a condom or other contraceptive device, a metered dose inhaler, a transdermal patch, an implantable pump, sponge, or other reservoir, or the like.

In some aspects, pharmaceutical compositions provided herein can be delivered via an intranasal spray, by inhalation, and/or by an aerosol. Methods for delivering pharmaceutical compositions directly to the lungs and/or nasal mucosa via nasal and/or pulmonary aerosols are well-known in the pharmaceutical arts. In further aspects, pharmaceutical compositions provided herein can be delivered ocularly, e.g., via eyedrops.

In some preferred aspects, pharmaceutical compositions provided herein are delivered via a liposomal nanoparticle formulation. For example, in some aspects, the compounds can be formulated within liposomes comprising a lipid bilayer formulated to enhance solubility and/or permeability across viral membranes. In further aspects, a liposomal nanoparticle formulation provided herein can comprise liposomes having a size range which facilitates delivery of the active compounds to viral membranes. Liposomal formulations can be prepared according to methods known to those skilled in the art.

Pharmaceutical compositions suitable for injectable use include sterile aqueous solutions (for water soluble compounds) or dispersions and sterile powders for the extemporaneous preparation of sterile injectable solutions or dispersions.

For intravenous administration, suitable carriers include, e.g., physiological saline, bacteriostatic water, Cremophor EL™ (BASF, Parsippany, N.J.) or phosphate buffered saline (PBS). The compositions are preferably sterile and fluid to allow for easy syringability.

Oral compositions generally include an inert diluent or an edible carrier, and can be incorporated with excipients in the form of tablets, troches, capsules, or the like. Oral compositions can also be prepared using a fluid carrier for use as a mouthwash or rinse wherein the compound in the fluid carrier is applied orally and swished and expectorated or swallowed. Tablets, pills, capsules, troches and the like can further comprise one or more of the following: binding agents, such as microcrystalline cellulose, gum tragacanth or gelatin; adjuvants, such as starch or lactose, disintegrating agents, such as alginic acid, Primogel, or corn starch; lubricants, such as magnesium stearate or Sterotes; glidants, such as colloidal silicon dioxide; and sweetening or flavoring agents, such as sucrose, saccharin, peppermint, methyl salicylate, or orange flavoring.

Pharmaceutical compositions provided herein are preferably stable under the conditions of manufacture and storage and preserved against the contaminating action of microorganisms such as bacteria and fungi. The carrier can be a solvent or dispersion medium containing, for example, water, ethanol, polyol (e.g., glycerol, propylene glycol, liquid polyetheylene glycol, or the like), and suitable mixtures thereof. The proper fluidity can be maintained, for example, by the use of a coating such as lecithin, by the maintenance of the required particle size in the case of a dispersion, and by the use of surfactants. Prevention of the action of microorganisms can be achieved by various antibacterial and antifungal agents, including, for example, parabens, chlorobutanol, phenol, ascorbic acid, thimerosal, and the like.

In some aspects, pharmaceutical compositions provided herein are formulated in dosage unit form (physically discrete units comprising a unitary, predetermined quantity of active compound calculated to produce the desired therapeutic effect in association with the required pharmaceutical carrier). The exact specifications of dosage unit forms will be dictated by the unique characteristics of the active compound, the particular therapeutic effect to be achieved, the preferred route of administration, and the like.

Toxicity and therapeutic efficacy antiviral compounds provided herein can be determined using standard pharmaceutical procedures in cell cultures or experimental animals. For example, established methods can be used to calculate $LD_{50}$ (the dose lethal to 50% of the population) and/or $ED_{50}$ (the dose therapeutically effective in 50% of the population) doses for the antiviral compounds. The dose ratio between toxic and therapeutic effects is the therapeutic index, which can be expressed as the ratio $LD_{50}/ED_{50}$. Compounds which exhibit large therapeutic indices are generally preferred, as are formulations and modes of administration which enhance the therapeutic index for a particular compound.

Data obtained from the cell culture assays and animal studies can be used in formulating a range of dosage for use in humans. In some aspects, dosages of antiviral compounds provided herein lie within a range of circulating concentrations which include the $ED_{50}$ with little or no toxicity. Dosages can vary within this range depending upon the dosage form, route of administration, and the like.

Therapeutically effective doses of compounds provided herein can be estimated initially from cell culture assays, e.g., based on the $IC_{50}$ (the concentration of a test compound which achieves a half-maximal inhibition of viral activity and/or infection). For example, the $IC_{50}$ observed in cell culture assays can be used to formulate a working dosage range for use in animal models in order to achieve a circulating plasma concentration range that includes the $IC_{50}$ with little or no toxicity. Conversion factors and calculation methods for converting animal dosages to human dose estimates are well known in the pharmaceutical arts. Concentrations of free compounds in plasma can be measured, for example, by high performance liquid chromatography.

As defined herein, a therapeutically effective amount of an antiviral compound provided herein (an effective dosage) can range from about 0.001 to 3000 mg/kg body weight, preferably from about 0.01 to 2500 mg/kg body weight, more preferably about 0.1 to 2000 mg/kg body weight, and even more preferably about 1 to 1000 mg/kg, 5 to 500 mg/kg, 10 to 100 mg/kg body weight. Skilled artisans will appreciate that a variety of factors can influence the dosage required to effectively treat a subject, including but not limited to the severity of the disease or condition being treated, history of previous treatments, general health and/or age of the subject, and the like. Accordingly, exact dosages for any particular subject will typically be determined empirically.

Pharmaceutical compositions provided herein can comprise a compound provided herein in an amount of at least 0.5% and generally not more than 90% by weight, based on the total weight of the composition, including excipients, if any. In some aspects, the proportion of antiviral agent varies between about 5-50% by weight of the composition.

Also provided herein are methods for treating or preventing infection by an enveloped virus, comprising administering an effective amount of a compound described herein to a subject in need of treatment.

As used herein, "treating" includes prevention, amelioration, alleviation, and/or elimination of a disease, disorder, or condition being treated or one or more symptoms of a disease, disorder, or condition being treated, as well as improvement in the overall well being of a patient, as measured by objective and/or subjective criteria.

In some aspects, the subject has been infected or is at risk of infection by an enveloped virus. A subject at risk of an enveloped virus infection can include any subject that has been exposed to or is likely to become exposed to an enveloped virus (e.g., via the skin or mucosal membranes). For example, subjects at risk can include medical providers, hospital staff and family members having contact with infected patients, as well as laboratory or quarantine facility workers having contact with samples, tissues, and like from infected patients.

In some aspects, the antiviral activity of a compound provided herein within a subject can be measured by assaying viral replication, viral infectivity, and/or viral load, and/or by measuring one or more secondary indicators of viral infection, such as indicators of inflammatory and/or immune responses.

Compounds and methods provided herein are useful for treating and preventing infections by any enveloped virus. "Enveloped" viruses are animal viruses having an outer membrane or 'envelope' comprised of a lipid bilayer with embedded viral proteins.

In some aspects, the enveloped virus is a type I Filoviridae virus which has a single-stranded, unsegmented (−) sense RNA genome and which causes severe hemorrhagic fever in humans and non-human primates. In some aspects, the Filoviridae virus is an Ebola virus, such as a Cote d'Ivoire (CI), Sudan (S), Zaire (Z) or Reston (R) species of Ebola virus. In further aspects, the Filoviridae virus is a Marburg virus.

In some aspects, the virus is an Orthomyxoviridae virus, such as an influenza virus, Thogotovirus, Dhori virus, or infectious salmon anemia virus. For example, in some aspects, methods provided herein are used to treat or prevent infection of a human subject with an influenza type A virus, an influenza type B virus, or an influenza type C virus. In some aspects, the influenza type A virus is of subtype H1N1, H2N2, H3N2 or H5N1.

In some aspects, the virus is a Paramyxoviridae virus, such as human parainfluenza virus, human respiratory syncytial virus (RSV), Sendai virus, Newcastle disease virus, mumps virus, rubeola (measles) virus, Hendra virus, Nipah virus, avian pneumovirus, or canine distemper virus.

In some aspects, the virus is a Rhabdoviridae virus, such as rabies virus, vesicular stomatitis virus (VSV), Mokola virus, Duvenhage virus, European bat virus, salmon infectious hematopoietic necrosis virus, viral hemorrhagic septicaemia virus, spring viremia of carp virus, or snakehead rhabdovirus.

In some aspects, the virus is a Bornaviridae virus, such as Borna disease virus.

In some aspects, the virus is a Bunyaviridae virus, such as Bunyamwera virus, Hantaan virus, Crimean Congo virus, California encephalitis virus, Rift Valley fever virus, or sandfly fever virus.

In some aspects, the virus is an Arenaviridae virus, such as Old World Arenaviruses, Lassa fever virus, Ippy virus, Lymphocytic choriomeningitis virus (LCMV), Mobala virus, Mopeia virus, or a New World Arenavirus, such as Junin virus (Argentine hemorrhagic fever), Sabia (Brazilian hemorrhagic fever), Amapari virus, Flexal virus, Guanarito virus (Venezuela hemorrhagic fever), Machupo virus (Bolivian hemorrhagic fever), Latino virus, Boliveros virus, Parana virus, Pichinde virus, Pirital virus, Tacaribe virus, Tamiami virus, or Whitewater Arroyo virus. In some aspects, the Arenaviridae virus is Lymphocytic choriomeningitis virus, Lassa virus, Junin Virus, Machupo Virus, Sabia virus, or Guanarito virus.

In some aspects, the virus is an arbovirus. Arboviruses comprise a large group of more than 400 enveloped RNA viruses that are transmitted primarily by arthropod vectors (e.g., mosquitoes, sand-flies, fleas, ticks, lice, etc). In some aspects, the arbovirus is a Togaviridae virus, such as an Alphavirus (e.g., Venezuela equine encephalitis virus or Sindbis virus) or a Rubivirus (e.g., Rubella virus). For example, in some aspects, a compound provided herein is administered to a pregnant subject to treat or prevent congenital rubella syndrome (CRS) and symptoms related thereto, such as low birth weight, deafness, and abortion.

In some aspects, the arbovirus is a Flaviviridae virus, such as a Flavivirus, a Pestivirus, a Hepadvirus, yellow fever virus, dengue fever virus, or Japanese encaphilitis (JE) virus.

In some aspects, the virus is a Hepacivirus, such as a hepatitis C virus or a hepatitis C-like virus.

In some aspects, the virus is a Henipavirus, such as Hendra virus or Nipah virus.

In further aspects, the virus is a Bunyaviridae (−)-sense RNA virus, such as an Orthobunyavirus, a Hantavirus, a Phlebovirus, or a Nairovirus.

In some aspects, the virus is a Arenavirius virus, such as Lymphocytic choriomeningitis virus (LCMV), Lassa virus, Junin virus, Machupo virus, or Guanarito virus.

In some aspects, the virus is a Japanese encephalitis virus, such as Alfuy virus, Japanese encephalitis virus, Kokobera virus, Koutango virus, Kunjin virus, Murray Valley encephalitis virus, St. Louis encephalitis virus, Stratford virus, Usutu virus, or West Nile virus.

In some aspects, the virus is human immunodeficiency virus (HIV).

In some aspects, the virus is a herpesvirus, for example, HSV-1 or HSV-2.

Also provided herein are methods of treating a disease or condition associated with an enveloped virus infection. For example, in some aspects, methods are provided herein for treating Ebola Hemorrhagic Fever (EHF), Marburg hemorrhagic fever (MHF), Dengue fever, Dengue hemorrhagic fever (DHF), yellow fever, dengue fever, acute and chronic hepatitis C, Venezuelan hemorrhagic fever, Brazilian hemorrhagic fever, Bolivian hemorrhagic fever, lymphocytic choriomeningitis, Lassa fever, hantavirus pulmonary syndrome (HPS), meningitis, influenza, AIDS, and/or genital herpes.

In some aspects, a compound provided herein is administered in combination with an antiviral agent or an antiviral vaccine.

Compounds and compositions provided herein can be administered in any amount and via any route of administration effective for attenuating infectivity of an enveloped virus. Exemplary routes of administration include, but are not limited to, oral, intrathecal, intra-arterial, direct bronchial application, parenteral (e.g., intravenous), intramuscular, intranasal, sublingual, intratracheal, inhalation, ocular, vaginal, and rectal administration.

The term effective amount refers to the amount necessary or sufficient to realize a desired biologic effect. As understood by those skilled in the art, an effective amount for any particular application can vary depending on such factors as the disease or condition being treated, the particular inhibitor being administered, the size of the subject, the severity of the disease or condition being treated, and/or other factors.

In some aspects, an effective amount of a compound provided herein is an amount that, when administered via a preferred mode of administration, is effective to treat or prevent viral infection in the subject without causing substantial toxicity or adverse side-effects. In further aspects, an effective amount of an antiviral compound provided herein is an amount which effectively inhibits fusion of an enveloped virus with the plasma membrane of a cell.

In additional aspects, an effective amount of an antiviral compound described herein is an amount which is effective to ameliorate one or more symptoms associated with an enveloped virus infection.

One of ordinary skill in the art can empirically determine effective amounts of antiviral compounds provided herein by routine experimentation.

In some aspects, methods are provided for preventing the spread of a sexually transmitted disease caused by an enveloped virus, such as but not limited to a herpesvirus (e.g., HSV-1 or HSV-2) or HIV, comprising administering an antiviral compound described herein to a subject who is at risk of being exposed to an enveloped virus. In some preferred aspects, the antiviral compound is administered as a topical formulation. In further preferred aspects, the antiviral compound is administered in conjunction with a device, such as but not limited to a condom or other contraceptive device.

In additional aspects, methods are provided for preventing infection due to an intentional exposure to an enveloped virus, for example related to biological warfare or terrorism, wherein the methods comprise administering an antiviral compound described herein to a subject who is at risk of being exposed to an enveloped virus.

Also provided herein are methods for inactivating enveloped viruses in a biological or pharmaceutical preparation, the methods comprising adding an antiviral compound provided herein to the preparation and incubating the mixture for a time sufficient to inactivate enveloped viruses present in the preparation.

In some preferred aspects, the antiviral compounds are substantially inert with respect to the structure and function of macromolecules, cells, tissues, organs and/or other biological structures comprising the preparation. For example, in some aspects, treating biological preparations with the antiviral compounds at a concentration and time sufficient to inactivate enveloped viruses within the preparation does not result in detectable protein denaturation, protein degradation, plasma membrane disruption, cell lysis, or the like.

In additional aspects, biological preparations treated with the antiviral compounds, at a concentration and time sufficient to inactivate enveloped viruses within the preparation, are substantially non-toxic to subjects to whom the preparations are intended for delivery, including but not limited to, human subjects. In some preferred aspects, biological preparations treated with the antiviral compounds are substantially non-toxic to human subjects without the need for further purification or processing.

In some aspects, the biological preparation is a biological sample drawn from a human or animal donor, such as but not limited to, blood, plasma, cerebrospinal fluid, mammary fluid, embryonic fluid, mucus, urine, and the like. For example, in some aspects, blood, tissue, or an organ harvested from a human or animal donor is treated according to methods provided herein to inactivate enveloped viruses, such as but not limited to HIV, prior to transplantation into a human or animal recipient. In some preferred aspects, the treated donor sample is transplanted into the recipient without removing the antiviral compound(s).

In further aspects, the biological preparation comprises cultured cells, tissues, or organs, such as but not limited to stem cells or xenographic tissues intended for transplantation. In additional aspects, the biological preparation comprises cultured host cells for the production of a recombinant protein or other biological product. In some preferred aspects, treating a cellular preparation with an antiviral compound provided herein inactivates enveloped viruses within the preparation without substantially affecting the growth, proliferation, viability, and/or productivity of the cells. In some preferred aspects, the treated cells are used or harvested without removing the antiviral compound(s).

Also provided herein are kits comprising a container housing an antiviral compound provided herein and instructions for administering the compound to a subject that has been infected or is at risk of infection by an enveloped virus. The instructions can provide for administration as an oral formulation, by inhalation, by topical administration, by intravenous injection and/or by any other suitable means.

In some aspects, kits provided herein optionally further comprise a pharmaceutical preparation vial and a pharmaceutically acceptable diluent, such as physiological saline for diluting a concentrated solution, salt or lyophilized powder formulation of an antiviral compound provided herein.

In some aspects, the kit comprises an inhaler for aerosolized administration to the lungs and/or upper respiratory tract. In further aspects, the kit comprises a device for intranasal administration to the nasal mucosa.

We have discovered that a recently developed series of pan-enveloped viral inhibitors, including but not limited to LJ001 and compounds of the formula IIIa and IVa, previously shown to prevent virus-cell membrane fusion and entry, are highly effective in inhibiting attachment, invasion and motility in *Toxoplasma gondii* and are useful as broad-spectrum antiparasitic agents. Motility and invasion are conserved processes in a wide array of related apicomplexan parasites, indicating that the compounds will be effective against this phylum of obligate intracellular parasites.

The antiparasitic activity reported herein suggests that the compounds block the release of parasite proteins from the secretory micronemes, opening an entirely new approach for controlling *Toxoplasma* and related parasites. Downstream events in invasion may also be affected (e.g., rhoptry release) as these similarly involve secretory membrane fusion events. Current anti-parasite therapies target biosynthetic pathways in the parasite and the bacterial-like apicoplast and are prone to mutations leading to resistance. The action of blocking membrane fusion processes provides a unique method of controlling this phylum of obligate intracellular parasites.

The processes of motility and invasion in *T. gondii* and related apicomplexan parasites require the release of adhesins from a specialized secretory organelle called the micronemes. As both motility and attachment are dramatically affected by the present compounds, the likely mechanism of inhibition is by disrupting fusion of the micronemes with the parasite plasma membrane and the subsequent release of adhesins. Additional steps downstream in the invasion process may also be affected (e.g., secretion from the rhoptries or dense granules which are other secretory organelles involved in invasion). The details of inhibition of motility and attachment are described in more detail herein.

The specific antiviral activity of the present compounds involves an ability to interact with the membranes of all lipid-enveloped viruses tested to date, and to disrupt subsequent virus-cell membrane fusion. As described herein, we have discovered that the present compounds also have antiparasitic activity relating to an ability to inhibit parasite attachment and invasion processes involving fusion of intracellular organellar membranes (in the parasite) with the plasma membrane.

In some aspects, compounds provided herein and derivatives thereof can be used for therapeutic treatment in humans or animals of (both acute and chronic) infections of a wide array of apicomplexan parasites.

In further aspects, compounds provided herein and derivatives thereof can be used as microbicides effective against infections in numerous insect hosts of apicomplexan parasites (e.g., mosquitoes, ticks).

Therapeutic intervention of apicomplexan parasites is generally focused on the inhibition of metabolic processes. Frequently targeted are the nucleotide salvage pathways (e.g., folate biosynthesis) or the apicoplast, a non-photosynthetic remnant of a chloroplast that is sensitive to certain antibiotics and is also involved in fatty acid and isoprenoid synthesis. Particularly troubling is the rapid rate of drug resistance (particularly in the malarial parasite *Plasmodium falciparum*), as well as the prohibitively high costs and toxicity of newly developed drugs. In addition, because the present compounds target membrane fusion events, it is highly likely to be effective against a wide array of these parasites and less likely to enable the parasites to develop resistance.

In spite of the conserved mechanism of host cell invasion in this phylum, current therapies do not target the invasive machinery which is composed of a parasite actin:myosin motor linked to organellar adhesins that are secreted at the onset of invasion. Small molecule screens have identified inhibitors of invasion (e.g., Carey K L et al, *Proc Natl Acad Sci USA*. 2004, 101:7433-8) but their precise targets and mechanism are unknown and they have not been utilized therapeutically in human or animal infections. Other inhibitors of invasion have been identified (Kato et al., *Nature Chemical Biology,* 4: 347-356 (2008)), but they are clearly distinct from the novel process identified here. These parasites do not have an extracellular life cycle, thus disruption of the invasive machinery is lethal.

The unique mechanism of inhibition of membrane fusion events described herein combined with data demonstrating the inhibition of *T. gondii* attachment and motility provides a novel approach for controlling apicomplexan parasites. Taken together, these data indicate that compounds provided herein act by inhibiting fusion of the *Toxoplasma* invasive organelles at the onset of host cell entry, arresting parasites in an extracellular environment in which they cannot survive. Existing therapies that target metabolic pathways or bacterial-like components of the apicoplast are prone to developing rapid drug resistance, thus compounds that targets lipid fusion events provide an attractive mechanism for targeting a wide array of these parasites and also avoiding rapid evolution of resistance.

Compounds provided herein are useful for inhibiting infections by other apicomplexan pathogens that affect humans (e.g., *Toxoplasma, Plasmodium* spp., *Cryptosporidium* spp., and *Isospora belli*) as well as pathogens of veterinary interest (e.g., *Theileria* spp, *Babesia* spp., *Eimeria* spp., *Neospora caninum*).

Also provided herein are methods for inactivating parasites in a biological or pharmaceutical preparation, the methods comprising adding an antiparasitic compound provided herein to the preparation and incubating the mixture for a time sufficient to inactivate parasites present in the preparation.

In some preferred aspects, the antiparasitic compounds are substantially inert with respect to the structure and function of macromolecules, cells, tissues, organs and/or other biological structures comprising the preparation. For example, in some aspects, treating biological preparations with the antiparasitic compounds at a concentration and time sufficient to inactivate parasites within the preparation does not result in detectable protein denaturation, protein degradation, plasma membrane disruption, cell lysis, or the like.

In additional aspects, biological preparations treated with the antiparasitic compounds, at a concentration and time sufficient to inactivate parasites within the preparation, are substantially non-toxic to subjects to whom the preparations are intended for delivery, including but not limited to, human subjects. In some preferred aspects, biological preparations treated with the antiparasitic compounds are substantially non-toxic to human subjects without the need for further purification or processing.

In some aspects, the biological preparation is a biological sample drawn from a human or animal donor, such as but not limited to, blood, plasma, cerebrospinal fluid, mammary fluid, embryonic fluid, mucus, urine, and the like. For example, in some aspects, blood, tissue, or an organ harvested from a human or animal donor is treated according to methods provided herein to inactivate parasites prior to transplantation into a human or animal recipient. In some preferred aspects, the treated donor sample is transplanted into the recipient without removing the antiparasitic compound(s).

In further aspects, the biological preparation comprises cultured cells, tissues, or organs, such as but not limited to stem cells or xenographic tissues intended for transplantation. In additional aspects, the biological preparation comprises cultured host cells for the production of a recombinant protein or other biological product. In some preferred aspects, treating a cellular preparation with an antiparasitic compound provided herein inactivates parasites within the preparation without substantially affecting the growth, proliferation, viability, and/or productivity of the cells. In some preferred aspects, the treated cells are used or harvested without removing the antiparasitic compound(s).

Also provided herein are kits comprising a container housing an antiparasitic compound provided herein and instructions for administering the compound to a subject that has been infected or is at risk of infection by a parasite. The instructions can provide for administration as an oral formulation, by inhalation, by topical administration, by intravenous injection and/or by any other suitable means.

In some aspects, kits provided herein optionally further comprise a pharmaceutical preparation vial and a pharmaceutically acceptable diluent, such as physiological saline for diluting a concentrated solution, salt or lyophilized powder formulation of an antiparasitic compound provided herein.

In some aspects, the kit comprises an inhaler for aerosolized administration to the lungs and/or upper respiratory tract. In further aspects, the kit comprises a device for intranasal administration to the nasal mucosa.

EXEMPLARY ASPECTS

Example 1

Compound Preparation

General Reaction (Z) 3-ethyl-5-(5-phenylfuran-2-ylmethyl-ene)oxazolidine-2,4-dithione 1 (JL102) and (Z) 3-ethyl-5-[5-(2-methoxyphenyl)-furan-2-ylmethylene]oxazolidine-2,4-dithione 2 (JL 103)

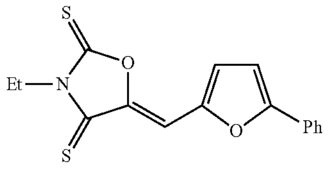

1 (JL102)

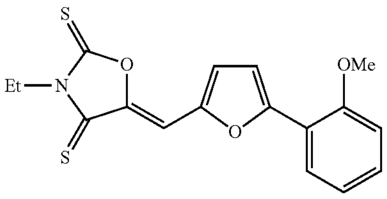

2 (JL103)

The two compounds were prepared from readily available materials as described in detail below. For compound 1 (JL102), the readily available ethyl 2-thioxooxazolidin-4-one 3 was reacted with the 5-phenyl-2-furfuraldehyde 4 in the presence of sodium acetate and acetic acid to produce the N-ethyl 5-(5-phenyl-2-furanylmethylene) 2-thioxooxazolidin-4-one 5 (JL101). Reaction of 5 with commercially available Lawesson's reagent in refluxing toluene afforded the desire oxazolidine-2,4-dithione 1 (JL102).

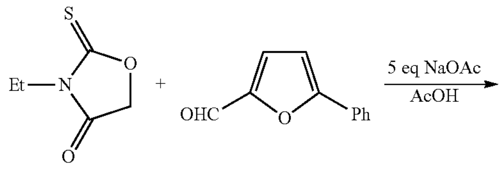

3

4

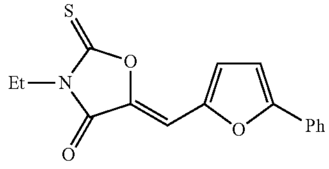

5 (JL101)

-continued

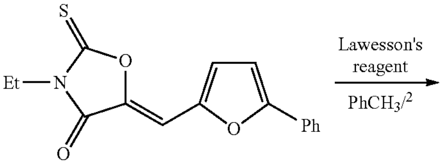

5 (JL101)

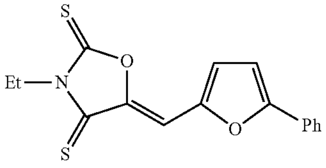

1 (JL102)

The second compound 2 (JL103) was prepared by similar chemistry. First the N-ethyl oxazolidine-2,4-dithione 6 was prepared from the 2-thioxooxazolidin-4-one 3 with Lawesson's reagent. Also the 5-(2-methoxyphenyl)-2-furfuraldehyde 9 was prepared by the Suzuki coupling of the bromide 7 with the boronic acid 8. Finally reaction of the N-ethyl oxazolidine-2,4-dithione 6 with the aldehyde 9 (using sodium acetate and acetic acid) gave the desired 5-arylmethylidene oxazolidine-2,4-dithione 2 (JL103). Many substituted derivatives of this class of compounds could be easily prepared by reaction of the N-substituted oxazolidine-2,4-dithiones 10 with various 5-aryl substituted 2-furfuraldehydes 11 using sodium acetate and acetic acid (or another base/acid combination) to give the desired N-substituted 5-arylmethylidene oxazolidine-2,4-dithiones 12.

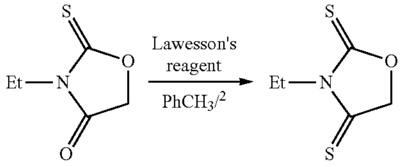

3

6

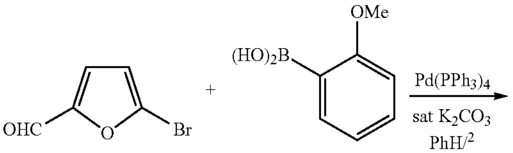

7

8

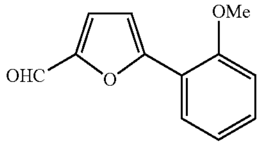

9

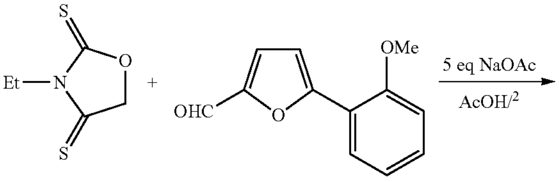

6

9

-continued

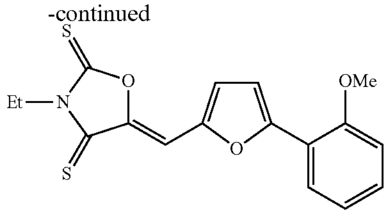

2 (JL103)

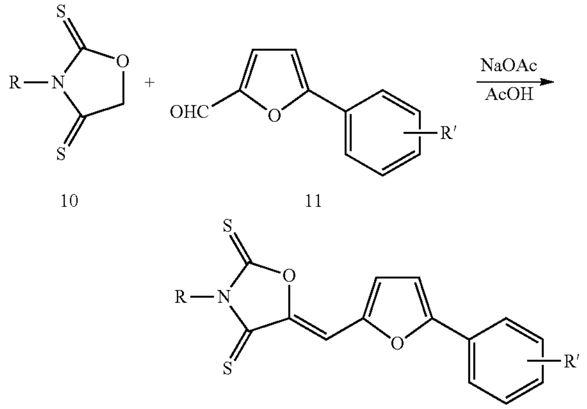

10 11

12

General Procedures

Materials were obtained from commercial suppliers and were used without further purification. Air or moisture sensitive reactions were conducted under argon atmosphere using oven-dried glassware and standard syringe/septa techniques. The reactions were monitored with a silica gel TLC plate under UV light (254 nm) followed by visualization with a p-anisaldehyde, ninhydrin, or Cerium Molybdate (Hanessian's stain) staining solution. Column chromatography was performed on silica gel 60. $^1$H NMR spectra were measured at 400 MHz in $CDCl_3$ unless stated otherwise and data were reported as follows in ppm (δ) from the internal standard (TMS, 0.0 ppm): chemical shift (multiplicity, integration, coupling constant in Hz.).

Preparation of (Z) 3-Ethyl-5-(5-phenylfuran-2-ylmethylene)-2-thioxooxazolidin-4-one 5 (JL101)

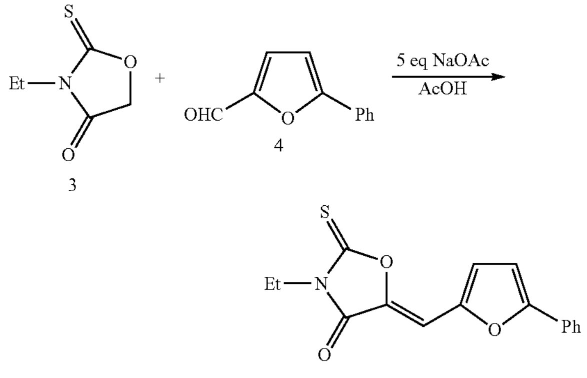

3 4

5 (JL101)

To a mixture of 3-ethyl-2-thioxooxazolidin-4-one 3 (145 mg, 1.0 mmol), 5-phenyl-2-furaldehyde 4 (172 mg, 1.0 mmol) and sodium acetate (410 mg, 5.0 mmol) was added acetic acid (5 mL). The reaction mixture was refluxed for 30 h, then the excess solvent was removed in vacuo. The residue was diluted with ethyl acetate (100 mL), then washed with water (2×20 mL). The organic layer was dried with brine and $MgSO_4$, then concentrated in vacuo. The desired product 5 (JL101) was obtained by recrystallization from an ethyl acetate/hexanes mixture in 45% yield (135 mg, light yellow needles). $^1$H NMR (400 MHz, $CDCl_3$): 7.81-7.76 (m, 2H), 7.44 (dt, J=8.0, 1.6 Hz), 7.36 (t, J=6.0 Hz, 1H), 7.28 (d, J=3.6 Hz, 1H), 6.88 (d, J=3.6 Hz, 1H), 6.80 (s, 1H), 3.97 (q, J=7.2 Hz, 2H), 1.34 (t, J=7.2 Hz, 3H).

Preparation of (Z) 3-Ethyl-5-(5-phenylfuran-2-ylmethylene)oxazolidine-2,4-dithione 1 (JL102)

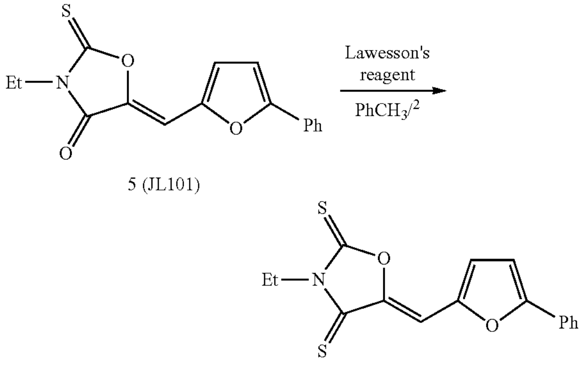

5 (JL101)

1 (JL102)

A toluene (3 mL) solution of 3-ethyl-5-(5-phenylfuran-2-ylmethylene)-2-thioxooxazolidin-4-one 5 (JL101) (88 mg, 0.29 mmol) and Lawesson's reagent (176 mg, 0.435 mmol) was refluxed overnight. The solution was cooled and diluted with ethyl acetate (50 mL), then washed with water (2×10 mL). The organic layer was dried with brine and $MgSO_4$, and concentrated in vacuo. The residue was purified by flash column chromatography on silica gel (hexane:ethyl acetate=20:1), and the desired product 1 (M102) was obtained in 82% yield (75 mg, red-orange solid). $^1$H NMR (400 MHz, $CDCl_3$): δ 7.80 (d, J=1.2 Hz, 2H), 7.46-7.36 (m, 4H), 7.05 (s, 1H), 6.91 (d, J=3.6 Hz, 1H), 4.30 (q, J=7.2 Hz, 2H), 1.34 (t, J=7.2 Hz, 3H); $^{13}$C NMR (100 MHz, $CDCl_3$): δ 182.8, 182.3, 158.5, 148.5, 147.0, 129.3, 129.1, 124.8, 122.3, 117.6, 109.9, 103.0, 41.7, 11.3 ppm; IR (NaCl) 2917, 2848, 1634, 1389, 1360, 1348, 1271, 1226, 1114, 1078, 1033, 953, 760, 691 $cm^{-1}$.

Preparation of 3-Ethyloxazolidine-2,4-dithione (6)

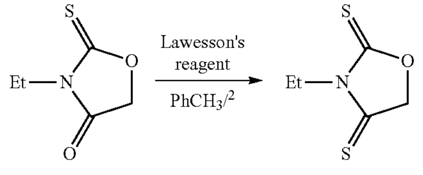

3 6

A toluene (10 mL) solution of 3-ethyl-2-thioxooxazolidin-4-one 3 (145 mg, 1.0 mmol) and Lawesson's reagent (607 mg, 1.5 mmol) was refluxed overnight. The solution was cooled and diluted with ethyl acetate (100 mL), then washed with water (2×20 mL). The organic layer was dried with brine and $MgSO_4$, and concentrated in vacuo. The residue was purified by flash column chromatography on silica gel (hexane:ethyl acetate=10:1), and the desired product 6 was obtained in 94% yield (152 mg, orange oil). $^1H$ NMR (400 MHz, $CDCl_3$): δ 5.12 (s, 2H), 4.21 (q, J=7.2 Hz, 2H), 1.29 (t, J=7.2 Hz, 3H).

Preparation of Aryl-2-Furaldehydes

Aryl-2-furaldehydes were generally prepared accordingly:

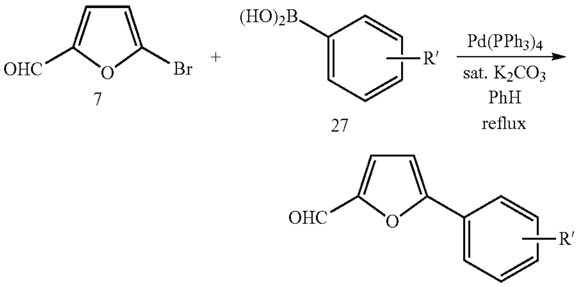

7

27

To a benzene (10 mL) solution of 5-bromo-2-furaldehyde 7 (350 mg, 2.0 mmol) and arylboronic acid 27 (2.0 mmol) was added tetrakis(triphenylphosphine)-palladium(0) (69.4 mg, 0.06 mmol) and sat. aq. $K_2CO_3$ solution (2.0 ml) at 21° C. under an argon atmosphere. The reaction mixture was refluxed for overnight. The mixture was then cooled and diluted with ethyl acetate (100 mL). The organic layer was washed with water (2×20 mL), then dried with brine and $MgSO_4$ and concentrated in vacuo. Flash column chromatography on silica gel (n-hexanes:ethyl acetate=20:1) of the residue afforded 5-aryl-2-furaldehyde.

The following compounds were prepared in accordance with the above scheme.

| | R' | Yield (%) |
|---|---|---|
| 9 | 2-methoxy | 65 |
| 28 | 4-methoxy | 78 |
| 29 | 2,4-dimethoxy | 58 |
| 30 | 2,3-dimethoxy | 80 |
| 31 | 2,6-dimethoxy | 26 |
| 32 | 3-methoxy | 87 |
| 33 | 4-dimethylamino | 66 |
| 34 | 2,4,6-trimethoxy | 32 |

Preparation of 5-(2-Methoxyphenyl)-2-Furaldehyde (9)

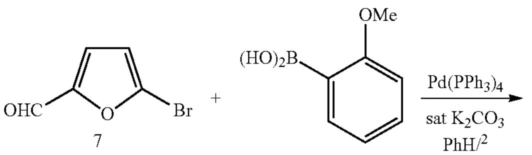

7

8

-continued

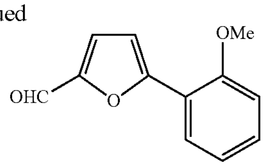

9

To a benzene (10 mL) solution of 5-bromo-2-furaldehyde 7 (350 mg, 2.0 mmol) and 2-methoxyphenylboronic acid 8 (304 mg, 2.0 mmol) was added tetrakis(triphenylphosphine)-palladium(0) (69.4 mg, 0.06 mmol) and sat. aq. $K_2CO_3$ solution (4.94 ml, 4.0 mmol) at 21° C. under an argon atmosphere. The reaction mixture was refluxed for 2 h. The mixture was then cooled and diluted with ethyl acetate (100 mL). The organic layer was washed with water (2×20 mL), then dried with brine and $MgSO_4$ and concentrated in vacuo. Flash column chromatography on silica gel (hexane:ethyl acetate=20:1) of the residue afforded 5-(2-methoxyphenyl)-2-furaldehyde 9 in 65% yield (265 mg, yellow oil). $^1H$ NMR (400 MHz, $CDCl_3$): δ 9.65 (s, 1H), 8.05 (dd, J=8.0, 2.0 Hz, 1H), 7.39-7.35 (m, 1H), 7.33 (d, J=3.6 Hz, 1H), 7.14 (d, J=4.0 Hz, 1H), 7.07 (dt, J=7.2, 0.8 Hz, 1H), 7.00 (bd, J=8.0 Hz, 1H), 3.97 (s, 3H).

Characterization data for compounds 28-34 are discussed below.

5-(4-Methoxyphenyl)-2-furaldehyde 28 yellow caramel. $^1H$ NMR (400 MHz, $CDCl_3$): δ 9.60 (s, 1H), 7.77 (d, J=8.8 Hz, 1H), 7.31 (d, J=3.6 Hz, 1H), 6.97 (d, J=8.8 Hz, 1H), 6.72 (d, J=3.6 Hz, 1H), 3.86 (s, 3H).

5-(2,4-Dimethoxyphenyl)-2-furaldehyde 29 yellow caramel. $^1H$ NMR (400 MHz, $CDCl_3$): δ 9.59 (s, 1H), 7.98 (d, J=8.8 Hz, 1H), 7.31 (d, J=3.6 Hz, 1H), 7.00 (d, J=3.6 Hz, 1H), 6.60 (dd, J=8.8, 2.4 Hz, 1H), 6.54 (d, J=2.4 Hz, 1H), 3.94 (s, 3H), 3.87 (s, 3H).

5-(2,3-Dimethoxyphenyl)-2-furaldehyde 30 light yellow caramel. $^1H$ NMR (400 MHz, $CDCl_3$): δ 9.66 (s, 1H), 7.59 (dd, J=8.0, 1.6 Hz, 1H), 7.34 (d, J=3.6 Hz, 1H), 7.18 (d, J=3.6 Hz, 1H), 7.15 (t, J=8.0 Hz, 1H), 6.97 (dd, J=8.0, 1.6 Hz, 1H), 3.91 (s, 3H), 3.89 (s, 3H).

5-(2,6-Dimethoxyphenyl)-2-furaldehyde 31 yellow caramel. $^1H$ NMR (400 MHz, $CDCl_3$): δ 9.66 (s, 1H), 7.35 (t, J=8.4 Hz, 1H), 7.34 (d, J=3.6 Hz, 1H), 6.74 (d, J=3.6 Hz, 1H), 6.63 (d, J=8.4 Hz, 2H), 3.83 (s, 6H).

5-(3-Methoxyphenyl)-2-furaldehyde 32 yellow oil. $^1H$ NMR (400 MHz, $CDCl_3$): δ 9.66 (s, 1H), 7.42-7.35 (m, 3H), 7.32 (d, J=3.6 Hz, 1H), 6.95 (ddd, J=8.0, 3.2, 0.8 Hz, 1H), 6.84 (d, J=3.6 Hz, 1H), 3.88 (s, 3H).

5-(4-Dimethoxyphenyl)-2-furaldehyde 33 light yellow solid. $^1H$ NMR (400 MHz, $CDCl_3$): δ 9.54 (s, 1H), 7.71 (d, J=8.8 Hz, 2H), 7.29 (d, J=3.6 Hz, 1H), 6.73 (d, J=8.8 Hz, 2H), 6.63 (d, J=3.6 Hz, 1H), 3.04 (s, 6H).

5-(2,4,6-Trimethoxyphenyl)-2-furaldehyde 34 yellow solid. $^{1}H$ NMR (400 MHz, $CDCl_3$): δ 9.62 (s, 1H), 7.32 (d, J=3.6 Hz, 1H), 6.68 (d, J=3.6 Hz, 1H), 6.18 (S, 2H), 3.86 (s, 3H), 3.82 (s, 6H).

Preparation of (Z)-3-Ethyl-5-(5-aryl-furan-2-ylmethylene)oxazolidine-2,4-dithiones (Z)-3-Ethyl-5-(5-aryl-furan-2-ylmethylene)oxazolidine-2,4-dithiones were generally prepared accordingly:

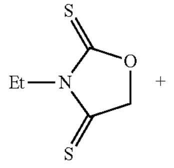
6

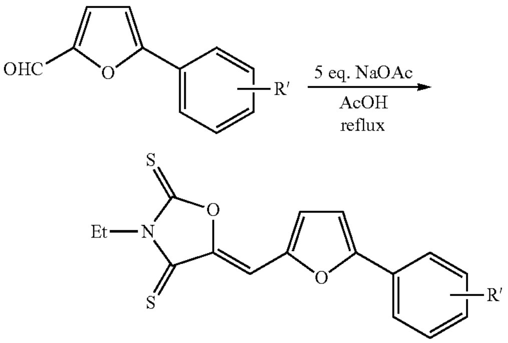

To a mixture of 3-ethyloxazolidine-2,4-dithione 6 (79 mg, 0.49 mmol), 5-(2-methoxyphenyl)-2-furaldehyde 9 (99 mg, 0.49 mmol) and sodium acetate (201 mg, 2.45 mmol) was added acetic acid (5 mL). As more of the desired product was formed, the reaction mixture color turned to a very dark red solution. The reaction mixture was refluxed overnight, then the excess solvent was removed in vacuo. The residue was diluted with ethyl acetate (100 mL), then washed with water (2×20 mL). The organic layer was dried with brine and $MgSO_4$, then concentrated in vacuo. The desired product was prepared by recrystallization from ethyl acetate/n-hexanes.

The following compounds were prepared in accordance with the above scheme.

| | | R' | Yield (%) |
|---|---|---|---|
| 1 | JL102 | H | 87 |
| 2 | JL103 | 2-methoxy | 95 |
| 16 | JL108 | 4-methoxy | 80 |
| 17 | JL109 | 2,4-dimethoxy | 93 |
| 18 | JL110 | 2,3-dimethoxy | 83 |
| 19 | JL111 | 2,6-dimethoxy | 90 |
| 22 | JL117 | 3-methoxy | 73 |
| 23 | JL118 | 4-dimethylamino | 70 |
| 26 | JL122 | 2,4,6-trimethoxy | 69 |

Preparation of (Z) 3-Ethyl-5-[5-(2-methoxyphenyl)-furan-2-ylmethylene]oxazolidine-2,4-dithione 2 (JL103)

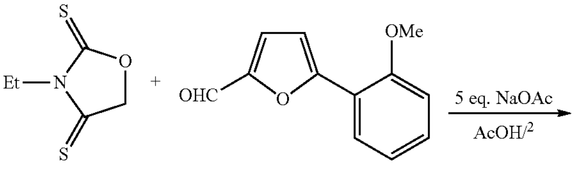

6 9

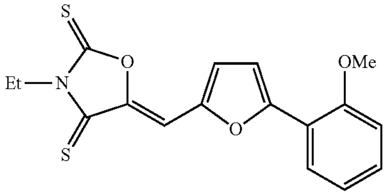
2 (JL103)

To a mixture of 3-ethyloxazolidine-2,4-dithione 6 (79 mg, 0.49 mmol), 5-(2-methoxyphenyl)-2-furaldehyde 9 (99 mg, 0.49 mmol) and sodium acetate (201 mg, 2.45 mmol) was added acetic acid (5 mL). As more of the desired product was formed, the reaction mixture color turned to a very red solution. The reaction mixture was refluxed overnight, then the excess solvent was removed in vacuo. The residue was diluted with ethyl acetate (100 mL), then washed with water (2×20 mL). The organic layer was dried with brine and $MgSO_4$, then concentrated in vacuo. Flash column chromatography afforded the desired product 2 (M103) in 95% yield (160 mg, purple solid).

$^{1}H$ NMR (400 MHz, $CDCl_3$): δ 7.98 (dd, J=8.0, 1.6 Hz, 1H), 7.37-7.33 (m, 2H), 7.19 (d, J=4.0 Hz, 1H), 7.08 (t, J=3.6 Hz, 1H), 7.05 (s, 1H), 6.98 (bd, J=8.4 Hz, 1H), 4.30 (q, J=7.2 Hz, 2H), 3.97 (s, 3H), 1.34 (t, J=7.2 Hz, 3H); $^{13}C$ NMR (100 MHz, $CDCl_3$): δ 182.6, 182.3, 156.5, 155.5, 147.5, 146.8, 130.2, 127.0, 122.9, 121.1, 118.3, 114.9, 111.2, 103.3, 55.5, 41.6, 11.3 ppm; IR (NaCl) 2967, 2921, 2845, 1622, 1505, 1486, 1391, 1351, 1304, 1271, 1245, 1114, 1078, 1022, 952, 788, 752 $cm^{-1}$; MS ($EI^+$): m/z 346 $[M+H]^+$; HRMS calculated for $C_{17}H_{15}NO_3S_2$: 345.0493. Found: 346.0544 $[M+H]^+$.

Characterization data for compounds 1, 16-19, 22, 23 and 26 are discussed below.

(Z)-3-Ethyl-5-(5-phenylfuran-2-ylmethylene)oxazolidine-2,4-dithione 1 (JL102)

red-orange solid. $^{1}H$ NMR (400 MHz, $CDCl_3$): δ 7.80 (d, J=1.2 Hz, 2H), 7.46-7.36 (m, 4H), 7.05 (s, 1H), 6.91 (d, J=3.6 Hz, 1H), 4.30 (q, J=7.2 Hz, 2H), 1.34 (t, J=7.2 Hz, 3H); $^{13}C$ NMR (100 MHz, $CDCl_3$): δ 182.8, 182.3, 158.5, 148.5, 147.0, 129.3, 129.1, 124.8, 122.3, 117.6, 109.9, 103.0, 41.7, 11.3 ppm; IR (NaCl) 2917, 2848, 1634, 1389, 1360, 1348, 1271, 1226, 1114, 1078, 1033, 953, 760, 691 $cm^{-1}$.

(Z)-3-Ethyl-5-[5-(2-methoxyphenyl)-furan-2-ylmethylene]oxazolidine-2,4-dithione 2 (JL103)

purple solid. $^{1}H$ NMR (400 MHz, $CDCl_3$): δ 7.98 (dd, J=8.0, 1.6 Hz, 1H), 7.37-7.33 (m, 2H), 7.19 (d, J=4.0 Hz, 1H), 7.08 (t, J=3.6 Hz, 1H), 7.05 (s, 1H), 6.98 (bd, J=8.4 Hz, 1H), 4.30 (q, J=7.2 Hz, 2H), 3.97 (s, 3H), 1.34 (t, J=7.2 Hz, 3H); $^{13}C$ NMR (100 MHz, $CDCl_3$): δ 182.6, 182.3, 156.5, 155.5, 147.5, 146.8, 130.2, 127.0, 122.9, 121.1, 118.3, 114.9, 111.2, 103.3, 55.5, 41.6, 11.3 ppm; IR (NaCl) 2967, 2921, 2845, 1622, 1505, 1486, 1391, 1351, 1304, 1271, 1245, 1114, 1078, 1022, 952, 788, 752 $cm^{-1}$; MS ($EI^+$): m/z 346 $[M+H]^+$; HRMS calculated for $C_{17}H_{15}NO_3S_2$: 345.0493. Found: 346.0544 $[M+H]^+$.

(Z)-3-Ethyl-5-(5-(4-methoxyphenyl)-furan-2-ylmethylene)oxazolidine-2,4-dithione 16 (JL108)

purple solid. $^1H$ NMR (400 MHz, $CDCl_3$): δ 7.74 (d, J=9.2 Hz, 2H), 7.36 (d, J=3.6 Hz, 1H), 7.06 (s, 1H), 6.98 (d, J=9.2 Hz, 2H), 6.80 (d, J=3.6 Hz, 1H), 4.30 (q, J=7.2 Hz, 2H), 3.87 (s, 3H), 1.35 (t, J=7.2 Hz, 3H).

(Z)-3-Ethyl-5-(5-(2,4-dimethoxyphenyl)-furan-2-ylmethylene)oxazolidine-2,4-dithione 17 (JL109)

dark purple solid. $^1H$ NMR (400 MHz, $CDCl_3$): δ 7.97 (d, J=4.0 Hz, 1H), 7.36 (d, J=3.6 Hz, 1H), 7.08 (d, J=3.6 Hz, 1H), 7.06 (s, 1H), 6.64 (dd, J=8.8, 2.4 Hz, 1H), 6.53 (d, J=2.4 Hz, 1H), 4.30 (q, J=7.2 Hz, 2H), 4.05 (s, 3H), 3.95 (s, 3H), 1.34 (t, J=7.2 Hz, 3H).

(Z)-3-Ethyl-5-(5-(2,3-dimethoxyphenyl)-furan-2-ylmethylene)oxazolidine-2,4-dithione 18 (JL110)

dark purple solid. $^1H$ NMR (400 MHz, $CDCl_3$): δ 7.55 (dd, J=8.0, 1.6 Hz, 1H), 7.38 (d, J=3.6 Hz, 1H), 7.23 (d, J=3.6 Hz, 1H), 7.17 (t, J=8.0 Hz, 1H), 7.05 (s, 1H), 6.95 (dd, J=8.0, 1.6 Hz, 1H), 4.31 (q, J=7.2 Hz, 2H), 3.92 (s, 3H), 3.90 (s, 3H), 1.35 (t, J=7.2 Hz, 3H).

(Z)-3-Ethyl-5-(5-(2,6-dimethoxyphenyl)-furan-2-ylmethylene)oxazolidine-2,4-dithione 19 (JL111)

dark purple solid. $^1H$ NMR (400 MHz, $CDCl_3$): δ 7.38 (d, J=3.6 Hz, 1H), 7.33 (t, J=8.4 Hz, 1H), 7.13 (s, 1H), 6.95 (d, J=3.6 Hz, 1H), 6.65 (d, J=8.4 Hz, 2H), 4.30 (q, J=7.2 Hz, 2H), 4.05 (s, 3H), 3.91 (s, 6H), 1.34 (t, J=7.2 Hz, 3H).

(Z)-3-Ethyl-5-(5-(3-methoxyphenyl)-furan-2-ylmethylene)oxazolidine-2,4-dithione 22 (JL117)

dark red solid. $^1H$ NMR (400 MHz, $CDCl_3$): δ 7.39-7.33 (m, 4H), 7.05 (s, 1H), 6.95-6.92 (m, 1H), 6.91 (d, J=3.6 Hz, 1H), 4.31 (q, J=7.2 Hz, 2H), 3.90 (s, 3H), 1.35 (t, J=7.2 Hz, 3H).

(Z)-3-Ethyl-5-(5-(4-dimethylaminophenyl)-furan-2-ylmethylene)oxazolidine-2,4-dithione 23 (JL118)

dark purple solid. $^1H$ NMR (400 MHz, $CDCl_3$): δ 7.68 (d, J=8.8 Hz, 2H), 7.38 (d, J=3.6 Hz, 1H), 7.07 (s, 1H), 6.76-6.73 (m, 3H), 4.30 (q, J=7.2 Hz, 2H), 3.05 (s, 6H), 1.35 (t, J=7.2 Hz, 3H).

(Z)-3-Ethyl-5-(5-(2,4,6-tiimethoxyphenyl)-furan-2-ylmethylene)oxazolidine-2,4-dithione 26 (JL122)

black solid. $^1H$ NMR (400 MHz, $CDCl_3$): δ 7.36 (d, J=3.6 Hz, 1H), 7.08 (s, 1H), 6.90 (d, J=3.6 Hz, 1H), 6.21 (s, 2H), 4.30 (q, J=7.2 Hz, 2H), 3.91 (s, 6H), 3.87 (s, 3H), 1.34 (t, J=7.2 Hz, 3H).

Preparation of JL104

JL104 was prepared from readily available materials according to the following scheme, as described in detail below. Similar compounds may also be prepared using this scheme.

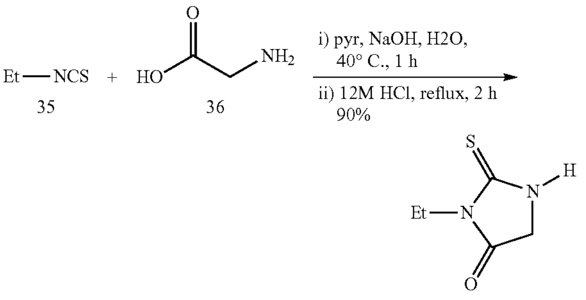

35 36 37

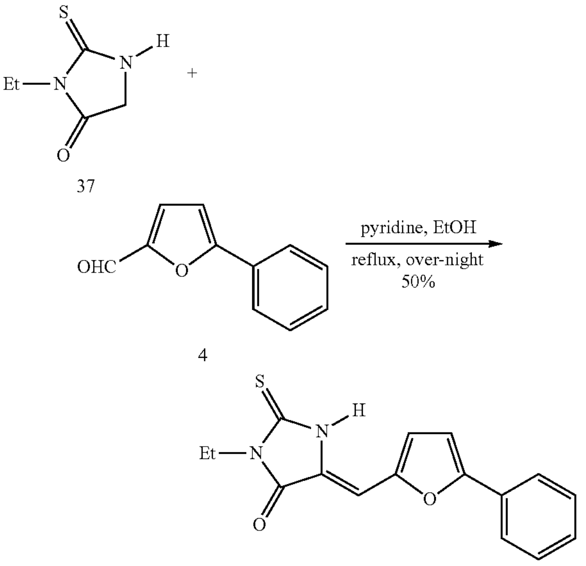

37 4 13 JL104

Preparation of 3-ethyl-2-thioxoimidazolidin-4-one 37

Glycine 36 (150 mg, 2.0 mmol) was dissolved in H2O (5.0 mL) and pyridine (5.0 mL) solution. The pH of the solution was adjusted to about 9.0 as shown by an indicator paper by the addition of 1M NaOH. The solution was heated to 40° C. and kept at that temperature during the reaction. Ethyl isothiocyanate 35 (0.263 mL, 3.0 mmol) was added with vigorous stirring. Small portions of 1M NaOH was added to keep the pH at about 9.0. The reaction was completed when the alkali consumption ceased (1 h). Pyridine and excess alkyl isothiocyanates were then removed by repeated extraction with equal volumes of benzene. Subsequently, an amount of conc. HCl (0.75 mL) was added and the mixture was refluxed for 2 h. The residue was extracted with ethyl acetate (2×150 mL). The organic layer was dried with brine and $MgSO_4$, then concentrated in vacuo. Flash column chromatography on silica gel (hexane:ethyl acetate=2:1) of the residue afforded the desired product 37 in 90% yield (258 mg, pale yellow solid). $^1H$ NMR (400 MHz, $CDCl_3$): 6.88 (br, 1H), 4.06 (d, J=1.2 Hz, 2H), 3.89 (q, J=7.2 Hz, 2H), 1.25 (t, J=7.2 Hz, 3H).

Preparation of (Z)-3-ethyl-5-((5-phenylfuran-2-yl)methylene)-2-thioxoimidazolidin-4-one 13 (JL104)

To an ethanol (10 mL) solution of 3-ethyl-2-thioxoimidazolidin-4-one 37 (145 mg, 1.0 mmol), 5-phenyl-2-furaldehyde 4 (172 mg, 1.0 mmol) was added pyridine (0.243 mL, 3.0 mmol). The reaction mixture was refluxed overnight, then the excess solvent was removed in vacuo. The residue was diluted with ethyl acetate (100 mL), then washed with water (2×20 mL). The organic layer was dried with brine and $MgSO_4$, then concentrated in vacuo. The desired product 13 (JL104) was obtained by recrystallization from an ethyl acetate/hexanes mixture in 50% yield (149 mg, yellow solid). $^1H$ NMR (400 MHz, $CDCl_3$): 9.16 (br, 1H), 7.69 (dd, J=7.2, 1.6 Hz, 2H), 7.49 (t, J=7.2 Hz, 2H), 7.41 (t, J=7.2 Hz, 1H), 6.52 (s, 1H), 4.00 (q, J=7.2 Hz, 2H), 1.31 (t, J=7.2 Hz, 3H).

Preparation of JL105

JL105 was prepared from readily available materials according to the following scheme, as described in detail below. Similar compounds may also be prepared using this scheme.

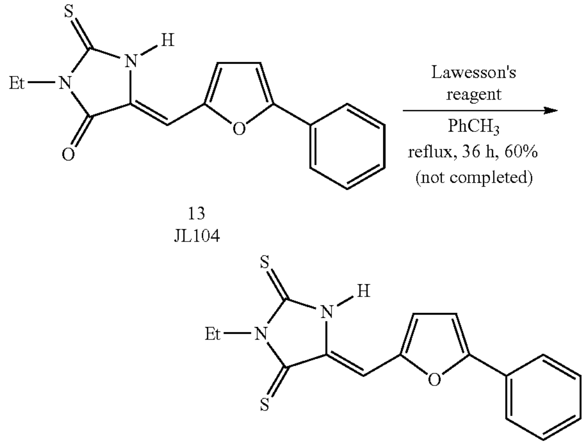

13
JL104

14
JL105

Preparation of (Z)-3-ethyl-5-((5-phenylfuran-2-yl)methylene)imidazolidine-2,4-dithione 14 (JL105)

A toluene (1 mL) solution of (Z)-3-ethyl-5-((5-phenylfuran-2-yl)methylene)-2-thioxoimidazolidin-4-one 13 (JL104) (30 mg, 0.1 mmol) and Lawesson's reagent (61 mg, 0.15 mmol) was refluxed overnight. The solution was cooled and diluted with ethyl acetate (50 mL), then washed with water (2×10 mL). The organic layer was dried with brine and $MgSO_4$, and concentrated in vacuo. The residue was purified by flash column chromatography on silica gel (n-hexanes: ethyl acetate=20:1), and the desired product 14 (JL105) was obtained in 89% yield (28 mg, red-orange solid). $^1H$ NMR (400 MHz, $CDCl_3$): δ 9.47 (br, 1H), 7.71 (d, J=7.2 Hz, 2H), 7.49 (t, J=7.2 Hz, 2H), 7.40 (t, J=7.2 Hz, 1H), 6.95 (d, J=3.6 Hz, 1H), 6.85 (d, J=3.6 Hz, 1H), 6.84 (s, 1H), 4.36 (q, J=7.2 Hz, 2H), 1.34 (t, J=7.2 Hz, 3H Preparation of JL107

JL107 was prepared from readily available materials according to the following scheme, as described in detail below. Similar compounds may also be prepared using this scheme.

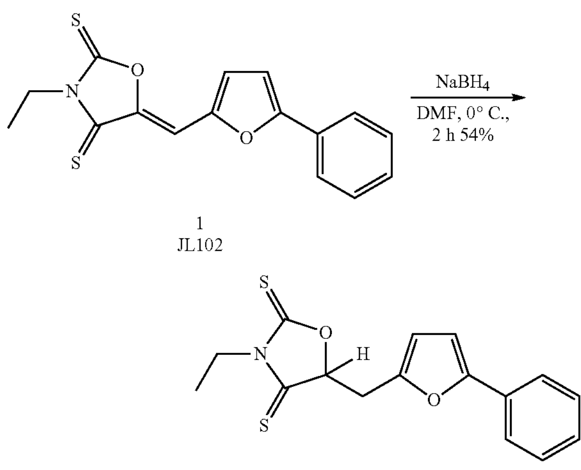

1
JL102

15
JL107

To a DMF (5 mL) solution of sodium borohydride (11.7 mg, 0.31 mmol) was added (Z)-3-Ethyl-5-(5-phenylfuran-2-ylmethylene)oxazolidine-2,4-dithione 1 (130 mg, 0.41 mmol) in DMF (2 mL) dropwise at 0° C. under argon atmosphere. As the reaction proceeded, the reaction mixture color was lightend to yellowish solution. The mixture was stirred for 1 h at 0° C. The reaction solution was poured into 1% aq. HCl, then extracted with ethyl acetate (2×50 mL). The organic layer was dried with brine and $MgSO_4$, and concentrated in vacuo. The residue was purified by flash column chromatography on silica gel (n-hexanes:ethyl acetate=30:1), and the desired product 15 (JL107) was obtained in 54% yield (70 mg, orange caramel). $^1H$ NMR (400 MHz, $CDCl_3$): δ 7.61 (d, J=7.2 Hz, 2H), 7.37 (t, J=7.2 Hz, 2H), 7.28-7.23 (m, 1H), 6.56 (d, J=3.2 Hz, 1H), 6.25 (d, J=3.2 Hz, 1H), 3.29 (dd, J=12.8, 6.8 Hz, 1H), 4.77 (dd, J=9.2, 3.6 Hz, 1H), 4.06 (qd, J=7.2, 3.6 Hz, 2H), 3.91 (dd, J=14.8, 3.2 Hz, 1H), 1.18 (t, J=7.2 Hz, 3H).

Preparation of JL113

JL113 was prepared from readily available materials according to the following scheme, as described in detail below. Similar compounds may also be prepared using this scheme.

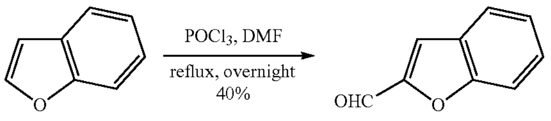

38 39

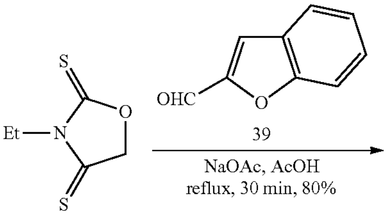

6

-continued

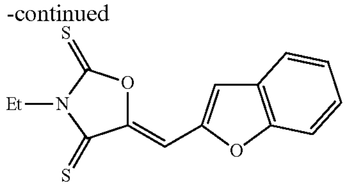

20
JL113

Preparation of 2,3-Benzofuran-5-carboxaldehyde 39

To a DMF (0.580 mL) solution of 2,3-benzofuran 38 (0.331 mL, 3.0 mmol) was added phosphorous oxychloride (0.302 mL, 3.3 mmol). The reaction mixture was stirred overnight at 80° C., then the excess solvent was removed in vacuo. The residue was diluted with ethyl acetate (100 mL), then washed with water (2×20 mL). The organic layer was dried with brine and $MgSO_4$, then concentrated in vacuo. Flash column chromatography on silica gel (n-hexanes:ethyl acetate=50:1) of the residue afforded the desired product 39 in 40% yield (172 mg, yellow oil). $^1H$ NMR (400 MHz, $CDCl_3$): 9.88 (s, 1H), 7.76 (d, J=7.2 Hz, 2H), 7.62 (dd, J=8.4, 0.8 Hz, 1H), 7.54 (d, J=0.8 Hz, 1H), 7.53 (td, J=7.2, 1.2 Hz, 1H), 7.35 (td, J=7.2, 0.8 Hz, 1H).

Preparation of (Z)-5-(benzofuran-2-ylmethylene)-3-ethyloxazolidine-2,4-dithione 20 (JL113)

To a mixture of 3-ethyloxazolidine-2,4-dithione 6 (100 mg, 0.62 mmol), 2,3-benzofuran-5-carboxaldehyde 39 (91 mg, 0.62 mmol) and sodium acetate (254 mg, 3.10 mmol) was added acetic acid (6 mL). The reaction mixture was refluxed for 1 h, then the excess solvent was removed in vacuo. The residue was diluted with ethyl acetate (70 mL), then washed with water (2×20 mL). The organic layer was dried with brine and $MgSO_4$, then concentrated in vacuo. Flash column chromatography on silica gel (n-hexanes:ethyl acetate=10:1) of the residue afforded the desired product 20 (JL113) in 80% yield (144 mg, red-orange solid). $^1H$ NMR (400 MHz, $CDCl_3$): 7.68 (d, J=3.6 Hz, 1H), 7.57 (s, 1H), 7.54 (dd, J=8.4, 0.8 Hz, 1H), 7.43 (td, J=7.2, 1.2 Hz, 1H), 7.29 (td, J=7.2, 1.2 Hz, 1H), 7.07 (s, 1H), 4.32 (q, J=7.2 Hz, 2H), 1.36 (t, J=7.2 Hz, 3H).

Preparation of JL119 and JL123 and Similar Compounds

JL119 and JL123 were prepared from readily available materials according to the following scheme, as described in detail below. Similar compounds may also be prepared using this scheme.

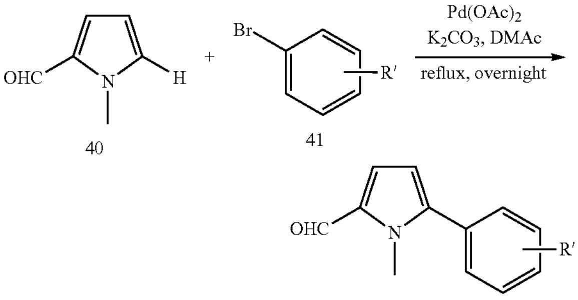

40 41 42

-continued

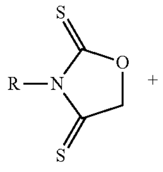

10

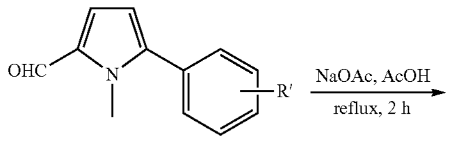

42

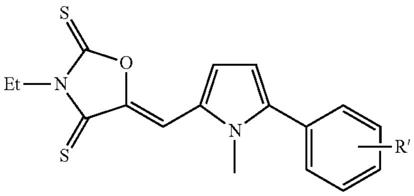

43

Preparation of 1-Methyl-5-aryl-1H-pyrrole-2-carboxaldehydes

1-Methyl-5-aryl-1H-pyrrole-2-carboxaldehydes were generally prepared accordingly:

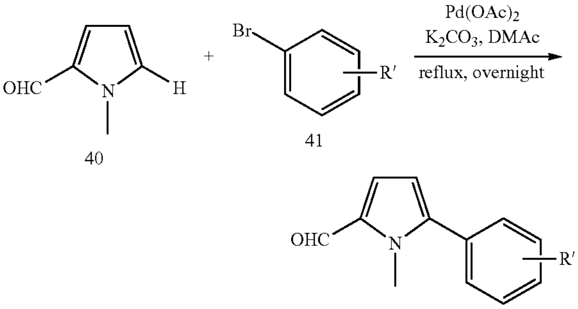

40 41 42

To a mixture of 1-methyl-2-pyrrole-carboxaldehyde 40 (0.408 mL. 4.0 mmol), substituted arylbromide (2.0 mmol), palladium diacetate (2.25 mg, 0.01 mmol) and $K_2CO_3$ (552 mg, 4.0 mmol) was added DMAc (6 mL) at 21° C. under an argon atmosphere. The reaction mixture was refluxed for overnight. The mixture was then cooled and diluted with ethyl acetate (100 mL). The organic layer was washed with water (2×20 mL), then dried with brine and $MgSO_4$ and concentrated in vacuo. Flash column chromatography on silica gel (n-hexanes:ethyl acetate=20:1) of the residue afforded 1-methyl-5-aryl-1H-pyrrole-2-carboxaldehyde.

The following compounds were prepared in accordance with the above scheme.

| | R' | Yield (%) |
|---|---|---|
| 44 | 4-methoxy | 60 |
| 45 | 4-dimethylamino | 20 |

Characterization data for compounds 44 and 45 are discussed below.

5-(4-Methoxyphenyl)-1-methyl-1H-pyrrole-2-carboxaldehyde 44

60% yield, pale yellow solid. $^1$H NMR (400 MHz, $CDCl_3$): δ 9.55 (s, 1H), 7.35 (d, J=8.8 Hz, 2H), 6.99 (d, J=8.8 Hz, 2H), 6.97 (d, J=4.0 Hz, 1H), 6.26 (d, J=4.0 Hz, 1H), 3.92 (s, 3H), 3.87 (s, 3H).

5-(4-Dimethylaminophenyl)-1-methyl-1H-pyrrole-2-carboxaldehyde 45

20% yield, brown solid. $^1$H NMR (400 MHz, $CDCl_3$): δ 9.51 (s, 1H), 7.30 (d, J=8.8 Hz, 2H), 6.95 (d, J=4.0 Hz, 1H), 6.77 (d, J=8.8 Hz, 2H), 6.24 (d, J=4.0 Hz, 1H), 3.94 (s, 3H), 3.02 (s, 6H).

Preparation of (Z)-3-Ethyl-5-((1-methyl-5-aryl-1H-pyrrole-2-yl)methylene)oxazolidine-2,4-dithiones (Z)-3-Ethyl-5-((1-methyl-5-aryl-1H-pyrrole-2-yl)methylene)oxazolidine-2,4-dithiones were generally prepared accordingly:

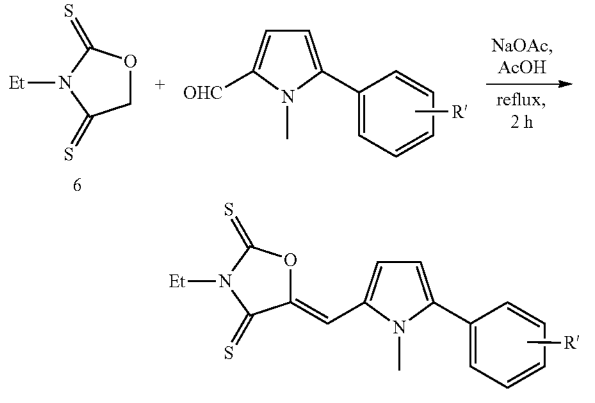

6

To a mixture of 3-ethyloxazolidine-2,4-dithione 6 (80 mg, 0.50 mmol), 1-Methyl-5-aryl-1H-pyrrole-2-carbox-aldehyde 42 (0.50 mmol) and sodium acetate (205 mg, 2.50 mmol) was added acetic acid (5 mL). As more of the desired product was formed, the reaction mixture color turned to a very dark solution. The reaction mixture was refluxed overnight, then the excess solvent was removed in vacuo. The residue was diluted with ethyl acetate (100 mL), then washed with water (2×20 mL). The organic layer was dried with brine and $MgSO_4$, then concentrated in vacuo. The desired product 43 was prepared by recrystallization from ethyl acetate/n-hexanes.

The following compounds were prepared in accordance with the above scheme.

| | | R' | Yield (%) |
|---|---|---|---|
| 23 | JL119 | 4-methoxy | 89 |
| 26 | JL123 | 4-dimethylamino | 48 |

Characterization data for compounds 23 (M119) and 45 (JL123) are discussed below.

(Z)-3-Ethyl-5-((5-(4-methoxyphenyl)-1-methyl-1H-pyrrole-2-yl)methylene)oxazolidine-2,4-dithione 23 (JL119)

dark purple solid. $^1$H NMR (400 MHz, $CDCl_3$): δ 7.46 (d, J=4.0 Hz, 1H), 7.36 (d, J=8.4 Hz, 2H), 7.11 (s, 1H), 7.00 (d, J=8.4 Hz, 2H), 6.44 (d, J=4.0 Hz, 1H), 4.31 (q, J=7.2 Hz, 2H), 3.87 (s, 3H), 3.76 (s, 3H), 1.36 (t, J=7.2 Hz, 3H).

(Z)-3-Ethyl-5-((5-(4-methoxyphenyl)-1-methyl-1H-pyrrole-2-yl)methylene)oxazolidine-2,4-dithione 26 (JL123)

black powder. $^1$H NMR (400 MHz, $CDCl_3$): δ 7.49 (d, J=4.4 Hz, 1H), 7.32 (d, J=8.8 Hz, 2H), 7.13 (s, 1H), 6.78 (d, J=8.8 Hz, 2H), 6.45 (d, J=4.4 Hz, 1H), 4.31 (q, J=7.2 Hz, 2H), 3.78 (s, 3H), 3.04 (s, 6H), 1.36 (t, J=7.2 Hz, 3H).

Preparation of JL121

JL121 was prepared from readily available materials according to the following scheme, as described in detail below. Similar compounds may also be prepared using this scheme.

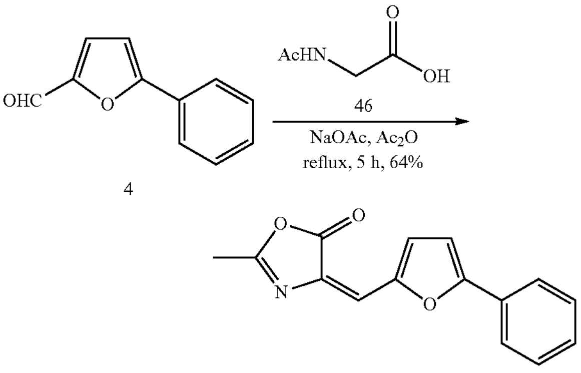

4

47

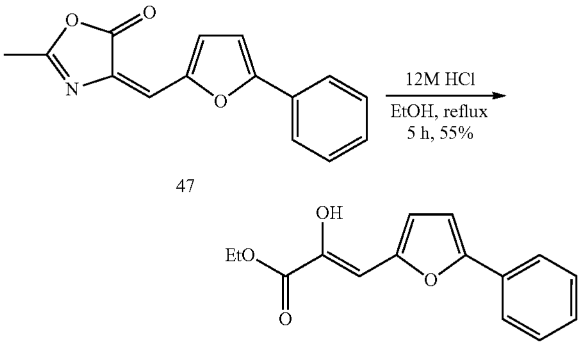

47

48

-continued

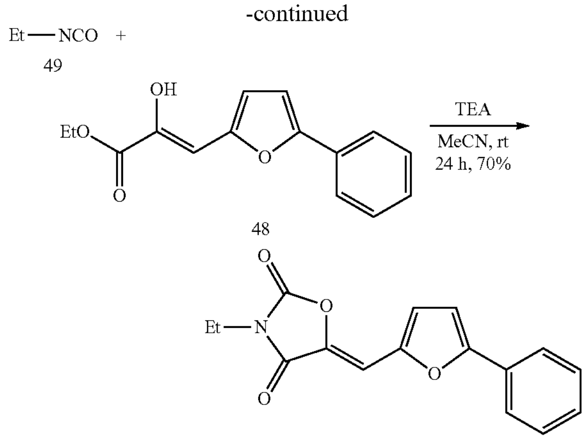

49

48

24

JL121

Preparation (E)-2-methyl-4-((5-phenylfuran-2-yl) methylene)oxazol-5(4H)-one 47 (JL120)

To a mixture of 5-phenyl-2-furaldehyde 4 (517 mg, 3.0 mmol), N-acetylglycine 46 (457 mg, 3.9 mmol) and sodium acetate (1230 mg, 15.0 mmol) was added acetic anhydride (30 mL). The reaction mixture was refluxed overnight, then the excess solvent was removed in vacuo. The residue was diluted with ethyl acetate (200 mL), then washed with water (2×50 mL). The organic layer was dried with brine and $MgSO_4$, then concentrated in vacuo. Flash column chromatography on silica gel (n-hexanes:ethyl acetate=10:1) of the residue afforded the desired product 47 (JL120) in 53% yield (400 mg, orange solid). $^1H$ NMR (400 MHz, $CDCl_3$): 7.77 (d, J=7.2 Hz, 2H), 7.52 (d, J=3.6 Hz, 1H), 7.44 (t, J=7.2 Hz, 2H), 7.35 (t, J=7.2 Hz, 1H), 7.12 (s, 1H), 6.89 (d, J=3.6 Hz, 1H), 2.41 (s, 3H).

Preparation (Z)-Ethyl 2-hydroxy-3-(5-phenylfuran-2-yl)acrylate 48

To an ethanol (10 mL) suspension of (E)-2-methyl-4-((5-phenylfuran-2-yl)methylene)oxazol-5(4H)-one 47 (253 mg, 1.0 mmol) was added 12M HCl (5 mL). The reaction mixture was refluxed for 5 h, then the excess solvent was removed in vacuo. The residue was diluted with ethyl acetate (100 mL), then washed with water (2×30 mL). The organic layer was dried with brine and $MgSO_4$, then concentrated in vacuo. Flash column chromatography on silica gel (n-hexanes:ethyl acetate=10:1) of the residue afforded the desired product 48 in 55% yield (142 mg, yellow solid). $^1H$ NMR (400 MHz, $CDCl_3$): 7.70 (d, J=7.2 Hz, 2H), 7.39 (t, J=7.2 Hz, 2H), 7.27 (t, J=7.2 Hz, 1H), 6.97 (d, J=3.6 Hz, 1H), 6.78 (d, J=3.6 Hz, 1H), 6.65 (d, J=1.6 Hz, 1H), 6.43 (d, J=1.6 Hz, 1H), 4.37 (q, J=7.2 Hz, 2H), 1.39 (t, J=7.2 Hz, 3H).

Preparation (Z)-3-ethyl-5-((5-phenylfuran-2-yl)methylene)oxazolidine-2,4-dione 24 (JL121)

To an MeCN (9 mL) solution of (Z)-Ethyl 2-hydroxy-3-(5-phenylfuran-2-yl)acrylate 48 (223 mg, 0.86 mmol) was added ethyl isocyanate 49 (0.136 mL, 1.72 mmol) and triethylamine (0.240 mL, 1.72 mmol). The reaction mixture was stirred for 24 h, then the excess solvent was removed in vacuo. The residue was diluted with ethyl acetate (100 mL), then washed with water (2×30 mL). The organic layer was dried with brine and $MgSO_4$, then concentrated in vacuo. Flash column chromatography on silica gel (n-hexanes:ethyl acetate=10:1) of the residue afforded the desired product 24 in 70% yield (310 mg, yellow solid). $^1H$ NMR (400 MHz, $CDCl_3$): 7.75 (d, J=7.2 Hz, 2H), 7.43 (t, J=7.2 Hz, 2H), 7.34 (t, J=7.2 Hz, 1H), 7.11 (d, J=3.6 Hz, 1H), 6.84 (d, J=3.6 Hz, 1H), 6.81 (s, 1H), 3.72 (q, J=7.2 Hz, 2H), 1.33 (t, J=7.2 Hz, 3H)); $^{13}C$ NMR (100 MHz, $CDCl_3$): δ 161.7, 160.0, 146.5, 128.9, 128.7, 124.5, 119.7, 118.0, 117.1, 116.9, 108.6, 101.9, 35.4, 13.1 ppm.

Example 2

Biological Methods

Characterization of the New Compounds

While conducting a high-throughput screen for small molecule inhibitors of Nipah virus (NiV) entry utilizing a pseudotyped vesicular stomatitis virus (VSV) system, a compound was discovered that not only inhibited VSVAG::rluc+ NiV-F/G pseudotype infection but also all subsequently tested enveloped virus, thus independently of the envelope protein used by the virus to enter the cells, but not non-enveloped viruses. This compound, a rhodanine derivative named LJ001, inhibits viral infection with an $IC_{50}$ of ~1 μM and an IC95 of ~10 μM common for all viruses tested [1]. A wide range of experiments allowed demonstrating that LJ001 (1) doesn't display overt toxicity in vitro or in vivo at concentrations of interest; (2) can prevent virus-induced mortality in vivo, when the viruses are pretreated with LJ001 before challenge in an animal; (3) LJ001 specifically acts on the viral membrane and prevent infection at a step after attachment but before virus-cell membranes fusion.

Structure-Activity relationship allowed the synthesis of new compounds with improved antiviral activity. Compound 1's $EC_{50}$ is about 10 fold lower than LJ001's, and compound 2's $EC_{50}$ about 10 fold lower than compound 1's as evaluated in an NDV infection assay of Vero cells (FIG. 1). Without being bound by any particular theory, it is presumed that the improved antiviral activity is attributed to better absorption of ambient light—the absorption peak of compound 2 is at about 500 nm whereas LJ001's is at about 440 nm, ambient light emitting most of its energy around 500 nm. Further, compound 2 absorbs more light (see Table 1, integrated area under the curve between 400 and 700 nm) than LJ001 (specifically, 1.53 times more). Finally, compound 2 has a higher quantum yield—i.e., the efficiency with which one photon absorbed from light produces its effect, (namely the generation of a singlet oxygen)—than LJ001 (see Table 1). Of note, the correlation of better absorption of light at longer wavelengths (see FIG. 5) and increased singlet oxygen quantum yield to increased antiviral activity (i.e., lower $IC_{50}$ values) (Table 1), is generally observed with respect to the compounds disclosed herein.

Figure 5:
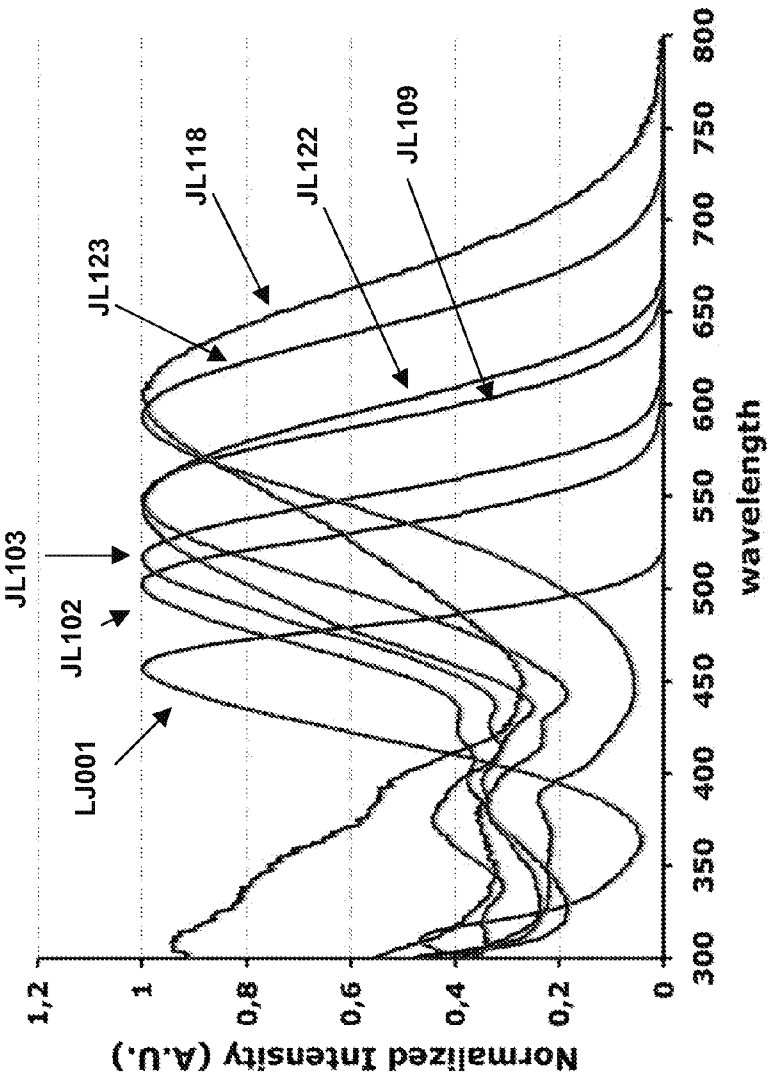
FIG. 5 shows the normalized absorption spectra of selected compounds in DMSO. The absorption spectra of 100 μM solutions of selected compounds in DMSO were scanned using a Tecan Infinite® M1000 microplate reader and normalized to their absorption maxima.

It is noted that the disclosed compounds are able to absorb light at a variety of wavelengths, with some compounds approaching near-infrared (NIR) (see Table 1, "Abs Max" and FIG. 5). Accordingly SAR of the disclosed compounds may uncover additional compounds which absorb light at high or even NIR wavelengths.

Cytotoxicity in the Presence of Light

Figure 2:
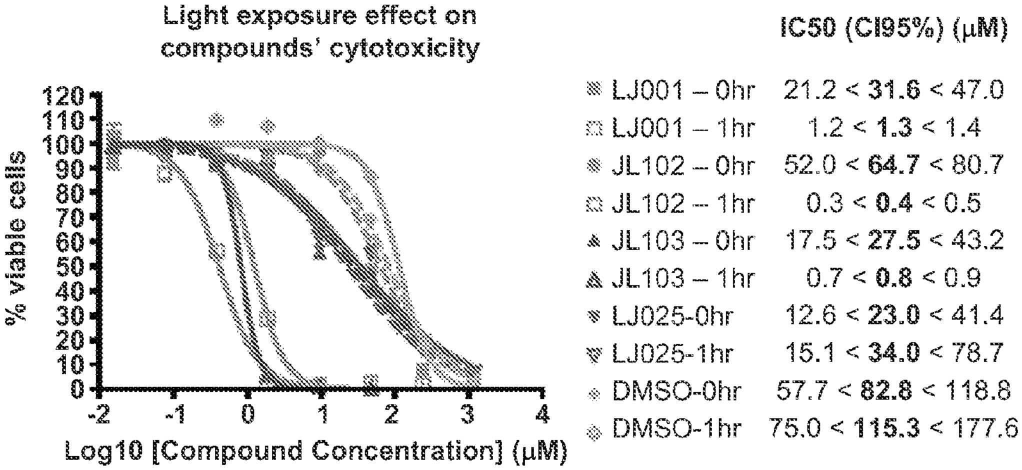
FIG. 2 shows increased cytotoxicity of the compounds under light exposure. Compounds at the indicated concentrations were incubated with Hela cells and left in the dark (0 hour, dashed lines) or exposed to light for 1 hour (solid lines). 24 hours later, cell survival was assessed by MTT assay. Inhibitory concentration 50% (IC50) and 95% confidence interval (CI95%) are indicated.

Cytotoxicity evaluated by the measurement of the number of remaining living cells (MTT) after treatment with the compound showed that when treated in the dark the compounds are not cytotoxic at concentrations below 10 μM (FIG. 2). However when exposed to light for different lengths of time the $EC_{50}$ decreases. As an example, when exposed for 1 hour to light the compound 1 triggers the death of 50% of the treated cells at a concentration of ~0.4 μM. Thus, the disclosed compounds exhibit high cytotoxicity at low concentrations upon light exposure, with toxicity increasing with the time of exposure.

Example 3

Antiviral Activity

The two examples of the oxazolidine-2,4-dithione class, JL102 and JL103 (1 and 2) have strong antiviral activity at nanomolar (nM) concentrations. These compounds are virucidal to lipid-enveloped viruses, i.e., those that have a lipid-membrane. In particular, we have shown that the compounds 1 and 2 inhibit the infection of various unrelated enveloped viruses, including Newcastle disease virus (NDV, paramyxovirus, as described in detail below and FIG. 1), human immunodeficiency virus (HIV, retrovirus), herpes simplex virus 1 (HSV-1, herpesvirus), cytomegalovirus (CMV, herpesvirus) and Semliki forest virus (SFV, alphavirus). Compounds 1 and 2 inhibit infection of each of these various unrelated enveloped viruses with approximately the same $IC_{50}$.

These compounds are generally effective against all lipid-enveloped viruses. The mechanism is expected to be the same as the one of rhodanine compounds we previously described [1]. In particular, we showed that this class of compounds (a) act on the virus at a much lower concentration than the one toxic for the host cells (FIG. 1 and FIG. 2), (b) irreversibly bind to the lipid membrane of enveloped viruses, (c) disrupt the integrity of lipid-enveloped viruses, and (d) renders treated viruses non-infectious under inhibitory concentrations that are non-cytotoxic. The mechanism of action is as follows: the non-polar (hydrophobic) right-hand part of the oxazolidinedithiones localizes the molecule preferentially in the non-polar hydrophobic lipid membrane environment; the incidence of normal ambient light photochemically activates the oxazolidinedithione molecule and induces formation of singlet oxygen from cellular oxygen which is likely to be concentrated in the lipid environment as well; the generation of singlet oxygen in the vicinity of the hydrophobic lipid membrane causes oxidative damage to the hydrophobic lipid chain and thereby disrupts the role of the lipid membrane through some as-yet unknown mechanism (destruction of the lipid chains, change in curvature of the membrane, change in polarity of the membrane, etc.).

Compound 1 shows remarkable inhibition of the infection of lipid-enveloped viruses, as previously mentioned, and at lower concentrations ($IC_{50}$~0.04 μM) than the previously described/claimed rhodanine derivatives [1]. Compound 2 shows even higher antiviral activity (roughly ten times more active than 1, $IC_{50}$~0.005 μM). Therefore both of these compounds (and perhaps their analogues) offer the potential for a better drug for the broad-spectrum treatment of viral infections, a potential antiviral topical or surface microbicide, as well as agents for pathogen inactivation in transfusion medicine. In addition, due to their specificity for lipid enveloped viruses, empiric response to the viral inhibitory properties of active compound 1 and its derivatives, can be used in the laboratory or clinical differential diagnosis of lipid-enveloped versus non-enveloped viruses.

Broad spectrum antivirals are rare. For example, ribavarin has activity against a few RNA virus by targeting RNA polymerase function [2], but it is not acutely virucidal (i.e. it does not kill the virus) and its efficacy varies tremendously when it does work. Furthermore, resistance can develop easily to almost any antiviral targeted against a viral protein. The in vitro $IC_{50}$ (inhibitory efficacy) of compound 1 is relatively similar for all the viruses tested, suggesting a common mechanism of action (as in targeting the viral lipid membrane). In addition, since compound 1 effectively targets the viral lipid membrane and not a viral protein, it is difficult for the virus to develop resistance even in principle. Moreover, since the effects target the lipid membrane rather than the genome (DNA or RNA) no mutagenic effect is expected. Finally, unlike many other photosensitizers that necessitate UV to be active, these compounds absorb in the visible light range spectrum, thus reducing the hazard associated with the use of UV light.

We previously carried out a wide-ranging array of biological assays that showed the potent antiviral activity of the rhodanine derivative that acts as a photosensitizer in the same way than the compounds herein described [1]. We have tested the previous compounds against enveloped and non-enveloped viruses encompassing several taxonomic orders, families, genera, and species. We have categorized the general mechanism of the compound's virucidal activity as functioning in modification or disruption of the enveloped virus' membrane, resulting in an irreversible inhibitory effect on the virus particle. In vitro toxicity assays indicate a relatively high therapeutic index with low cellular toxicity levels at antiviral concentrations. We also tested the toxicity, efficacy, and pharmacokinetics of the compounds in vivo in mouse dosing and viral challenge models. The first mouse challenge experiment indicated that the previous compound protected 100% of mice from lethal Rift Valley Fever Virus challenge compared to the vehicle (DMSO) control and an inactive analog (n=5 in each group). See [1] for details. We now showed that: (1) the compound 1 and its derivatives (compound 2 and other derivatives) are more effective than the rhodanine derivatives; (2) antioxidants can protect from the effects of the generated of singlet oxygen; (3) this class of photosensitizers can show high cytotoxicity at low concentrations upon light exposure, toxicity increasing with the time of exposure. We are evaluating whether chemiluminescence can be used to activate these compounds in a dark environment, and in vivo models of application (antiviral). For example, association of the oxazolidinedithiones with a system for local cellular light generation, e.g., coupling with an enzyme such as luciferase and then addition of luciferin, might provide the energy necessary to generate singlet oxygen intracellularly and thereby produce in vivo antiviral activity. Alternatively, organic nanocrystals (sodium yttrium fluoride based) have been developed that are capable of near-infrared to visible upconversion fluorescence. Such nanocrystals have been coated with photosensitizers and activation by tissue-penetrating near IR wavelengths can lead to singlet oxygen generation and apoptosis of cancer cells targeted with these nanocrystals (Guo H et al, Nanomedicine. 2010 Jan. 4. [Epub ahead of print]; Bechet et al "Nanoparticles as vehicles for delivery of photodynamic therapy agents" *Trends in Biotechnology,* 26:612-21). If our new series of active oxazolidine-2,4-dithiones can be conjugated to these upconverting nanocrystals, tissue penetrating near-IR light could be used to control activation of our antiviral in vivo.

The specific antiviral activity of compounds 1 and 2 involves their ability to interact with and disrupt the membrane integrity of all lipid-enveloped viruses tested to date. Several uses are possible. For example, the active compound(s) and its derivatives can be used for therapeutic treatment of active viral infections (with lipid-enveloped viruses). This can include acute or chronic treatment with the compound depending on the pathogenic profile of the virus.

The compound(s) and its derivatives can also be used for differential diagnosis between lipid enveloped versus non-enveloped viruses in an in vitro or in vivo setting against known or unknown viruses. For example, inhibition of virus infection or virus induced cytopathic effect with the compound will indicate that the pathogen in question is a lipid-enveloped virus, and will help guide further diagnostic steps. The active compound(s) and its derivatives can also be used for a topical microbicide that might be effective against mucosally transmitted lipid enveloped viruses such as HIV and Herpes Simplex Virus (HSV-1 and -2). The active compound(s) and its derivatives can also be used as sterilizing agents or decontaminants of blood products. The active compound(s) and its derivatives can also be used as sterilizing agents or decontaminants of surfaces.

We have also shown that compounds 1 and 2 (and perhaps their analogues) are more effective against HIV, NDV and HSV than rhodanine derivatives, with $IC_{50}$'s in the nanomolar range (see Table 1, "$IC_{50}$'s"). Other disclosed compounds similarly show improved efficacy against HIV, NDV and/or HSV (see also Table 1). In addition, we have also shown that compounds 1 and 2 (and perhaps their analogues) generate more singlet oxygen (increased quantum yield) than rhodanine derivatives (see Table 1, "1O2 QY"). Other disclosed compounds similarly demonstrate improved generation of singlet oxygen.

TABLE 1

| Name | Structure | IC50 ± STD (nM) (N = x) HIV | HSV | NDV | Abs Max (nm) | Relative integrated area from 400 to 700 nm | 1O2 QY 532 nm | 355 nm | KT × $10^{-7}$ ($M^{-1}s^{-1}$) |
|---|---|---|---|---|---|---|---|---|---|
| JL101 | 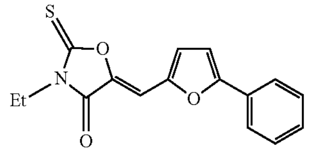 [SMILES: CCN1C(=O)/C(=C/c2ccc(-c3ccccc3)o2)OC1=S] | >1,000 (2) | | >1,000 (3) | | | | | |
| JL102 | 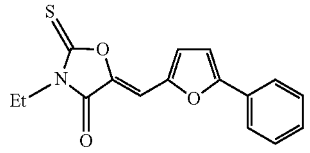 [SMILES: CCN1C(=O)/C(=C/c2ccc(-c3ccccc3)o2)OC1=S] | 60 ± 63 (5) | 2.8 ± 1.8 (3) | 35 ± 17 (6) | 501 | 134 | 0.08 ± 0.05 | 0.53 ± 0.04 | 16.0 ± 0.8 |
| JL103 | 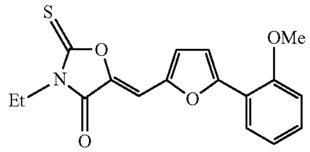 [SMILES: CCN1C(=O)/C(=C/c2ccc(-c3ccccc3OC)o2)OC1=S] | 3 ± 0 (1) | 2.3 ± 2.7 (4) | 7 ± 7 (11) | 516 | 153 | 0.63 ± 0.03 | 0.48 ± 0.02 | 7.8 ± 0.6 |
| JL104 | 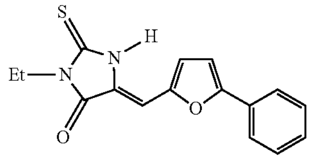 [SMILES: CCN1C(=O)/C(=C/c2ccc(-c3ccccc3)o2)NC1=S] | Not active | >500,000 (1) | >500,000 (2) | | | | | |
| JL105 | 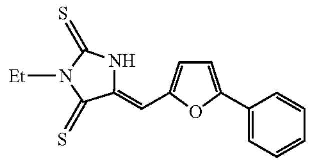 [SMILES: CCN1C(=S)N/C(=C\c2ccc(-c3ccccc3)o2)C1=S] | | | >100,000 (3) | 521 | | | | |
| JL107 | 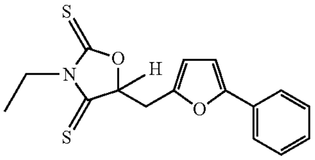 [SMILES: CCN1C(=S)OC(Cc2ccc(-c3ccccc3)o2)C1=S] | | | 928 ± 432 (2) | | | | | |

TABLE 1-continued
| Name | Structure | IC50 ± STD (nM) (N = x) HIV | HSV | NDV | Abs Max (nm) | Relative integrated area from 400 to 700 nm | 102 QY 532 nm | 102 QY 355 nm | KT × $10^{-7}$ ($M^{-1}s^{-1}$) |
|---|---|---|---|---|---|---|---|---|---|
| JL108 | 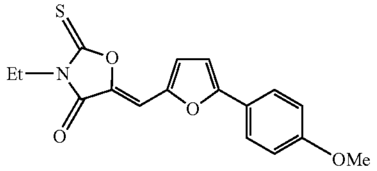 [SMILES: CCN1C(=O)/C(=C/c2ccc(-c3ccc(OC)cc3)o2)OC1=S] | | | 5 ± 3 (4) | 526 | 188 | 0.52 ± 0.03 | 0.53 ± 0.03 | 4.9 ± 0.4 |
| JL109 | 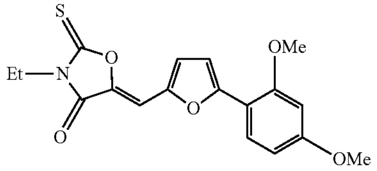 [SMILES: CCN1C(=O)/C(=C/c2ccc(-c3ccc(OC)cc3OC)o2)OC1=S] | | 0.8 ± 0.6 (2) | 4 ± 4 (6) | 550 | 178 | 0.38 ± 0.02 | 0.37 ± 0.02 | 2.0 ± 0.1 |
| JL110 | 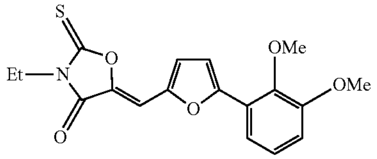 [SMILES: CCN1C(=O)/C(=C/c2ccc(-c3cccc(OC)c3OC)o2)OC1=S] | | | 127 ± 101 (4) | | | | | |
| JL111 | 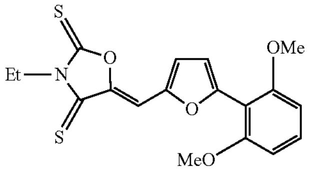 [SMILES: CCN1C(=S)O/C(=C\c2ccc(-c3c(OC)cccc3OC)o2)C1=S] | | | 12 ± 1 (3) | 499 | | | | |
| JL113 | 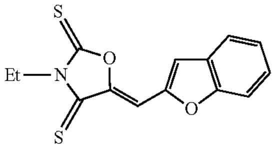 [SMILES: CCN1C(=S)O/C(=C\c2cc3ccccc3o2)C1=S] | | | 865 ± 519 (2) | | | | | |
| JL117 | 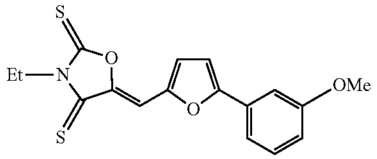 [SMILES: CCN1C(=S)O/C(=C\c2ccc(-c3cccc(OC)c3)o2)C1=S] | | 20 ± 0 (1) | 5 ± 3 (2) | 504 | | | | |
| JL118 | 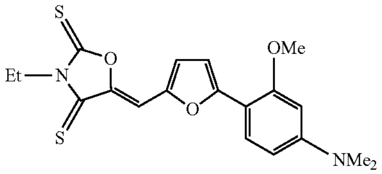 [SMILES: CCN1C(=S)O/C(=C\c2ccc(-c3ccc(N(C)C)cc3OC)o2)C1=S] | | | 2 ± 1 (4) | 606 | 200 | 0.15 ± 0.02 | 0.14 ± 0.01 | 4.6 ± 0.3 |
| JL119 | 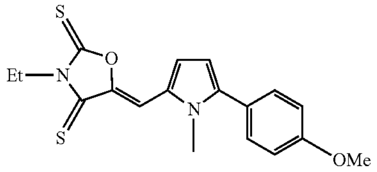 [SMILES: CCN1C(=S)O/C(=C\c2ccc(-c3ccc(OC)cc3)n2C)C1=S] | | | 6 ± 2 (3) | 551 | | | | |

TABLE 1-continued

| Name | Structure | IC50 ± STD (nM) (N = x) HIV | HSV | NDV | Abs Max (nm) | Relative integrated area from 400 to 700 nm | 102 QY 532 nm | 102 QY 355 nm | KT × $10^{-7}$ ($M^{-1}s^{-1}$) |
|---|---|---|---|---|---|---|---|---|---|
| JL121 | 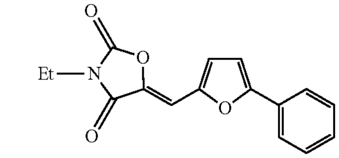 [SMILES: CCN1C(=O)O/C(=C\c2ccc(-c3ccccc3)o2)C1=O] | | Not active (1) | >500,000 (2) | | | 0 | 0 | 2.5 ± 0.2 |
| JL122 | 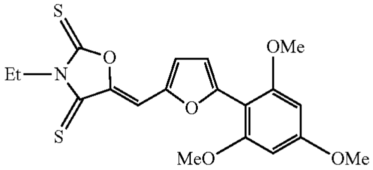 [SMILES: CCN1C(=S)O/C(=C\c2ccc(-c3c(OC)cc(OC)cc3OC)o2)C1=S] | | 3 ± 1 (2) | 1 (1) | 547 | | | | |
| JL123 | 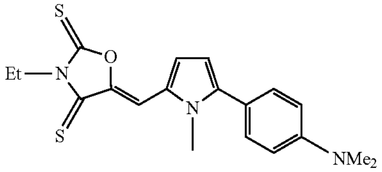 [SMILES: CCN1C(=S)O/C(=C\c2ccc(-c3ccc(N(C)C)cc3)n2C)C1=S] | | 75 ± 45 (2) | 49 (1) | 593 | | | | |
| JL001 | 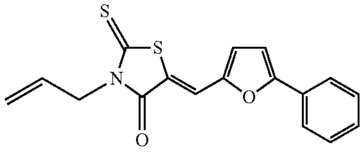 [SMILES: C=CCN1C(=O)/C(=C/c2ccc(-c3ccccc3)o2)SC1=S] | 183 ± 272 (9) | 35 ± 48 (3) | 207 ± 110 (10) | 457 | 100 | 0 | 0.35 ± 0.03 | 1.0 ± 0.1 |
| JL025 | 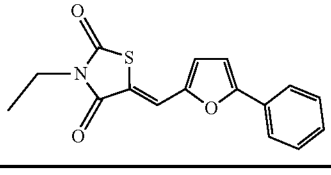 | Not active (4) | Not active (1) | Not active (2) | 405 | | | | |

Notably, compounds 1 and 2 (and perhaps their analogues exhibit) less toxicity and higher bioavailability in vivo, when compared to the rhodanine derivatives, after either gavage or intravenous or intraperitoneal administration in mice.

The pharmacokinetic (PK) profile of LJ-001, JL-102 and JL-103 was determined after a single oral gavage (po), intraperitoneal (ip) or intravenous (iv) administration to female Balb/c mice.

Mice were treated with a single dose of the 3 test articles at 10 mg/kg iv, ip and po, and 100 mg/kg po. In the 3 iv dose groups, clinical signs, including tremors, hypoactivity or rough fur, were observed in some of the mice. Out of the first 3 mice treated with LJ-001 at 10 mg/kg ip, 2 were sacrificed in moribund condition and 1 was found dead shortly after dose administration. These mice were replaced and the dose level was reduced to 5 mg/kg. Mice treated with LJ-001 at 5 mg/kg ip, and JL-102 and JL103 at 10 mg/kg ip appeared normal. Hypoactivity was the only clinical observation noted in some of the mice treated with the 3 test articles at 10 and 100 mg/kg po.

LJ-001 (10 mg/kg iv, 5 mg/kg ip, 10 and 100 mg/kg po) showed minimal exposure due in part to a very short half-life (0.2 hr) and fast elimination (~42000 ml/hr/kg). Oral bioavailability was not determined as there was only one plasma data point in each po dose group. JL-102 (10 mg/kg iv, 10 mg/kg ip, 10 and 100 mg/kg po) and JL-103 (10 mg/kg iv, 10 mg/kg ip, 10 and 100 mg/kg po) had comparable plasma time courses but the PK parameters showed differences specific to dose route and level. The 10 mg/kg po groups for JL-102 and JL-103 showed unexpectedly lower exposure than the 100 mg/kg po groups, possibly due to significant precipitation in the GI tract for the high dose levels. The ip bioavailability for JL-102 and JL-103 was near 50% but the po bioavailability ranged from 3.1 to 104.7%. The three drugs distributed well into tissues.

Example 4

Inhibition of Antiviral Activity by Antioxidants

Figure 3:
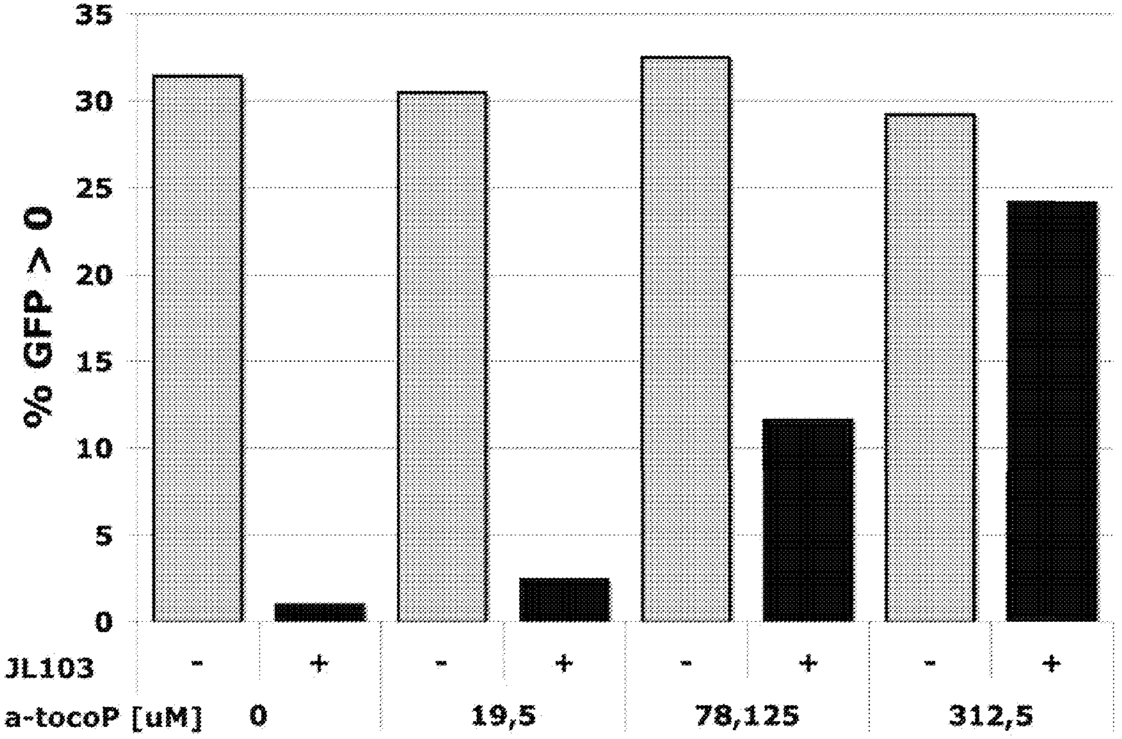
FIG. 3 shows that alpha-tocopherol blocks the antiviral activity of JL103 (compound 2). NDV virus encoding GFP was incubated with or without JL103 in the presence of increasing concentrations of alpha-tocopherol. Vero cells were then infected with the virus. At 24 h post-infection, cells were harvested and GFP expression was measured by flow cytometry.

It has been observed that antioxidants (e.g., alpha-tocopherol) offer protection from the antiviral effects of the generated singlet oxygen. The ability of the antioxidant alpha-tocopherol (a form of vitamin E) to protect viruses from the antiviral activity of compound 2 was evaluated using NDV virus. NDV was preincubated with increasing concentrations of alpha-tocopherol and then treated with 15 nM (≈$EC_{90}$) of compound 2, which maintains its ability to infect cells even when the appropriate amount of alpha-tocopherol is provided (see FIG. 3).

Example 5

HIV Inactivation in Packed Red Blood Cells

Figure 4:
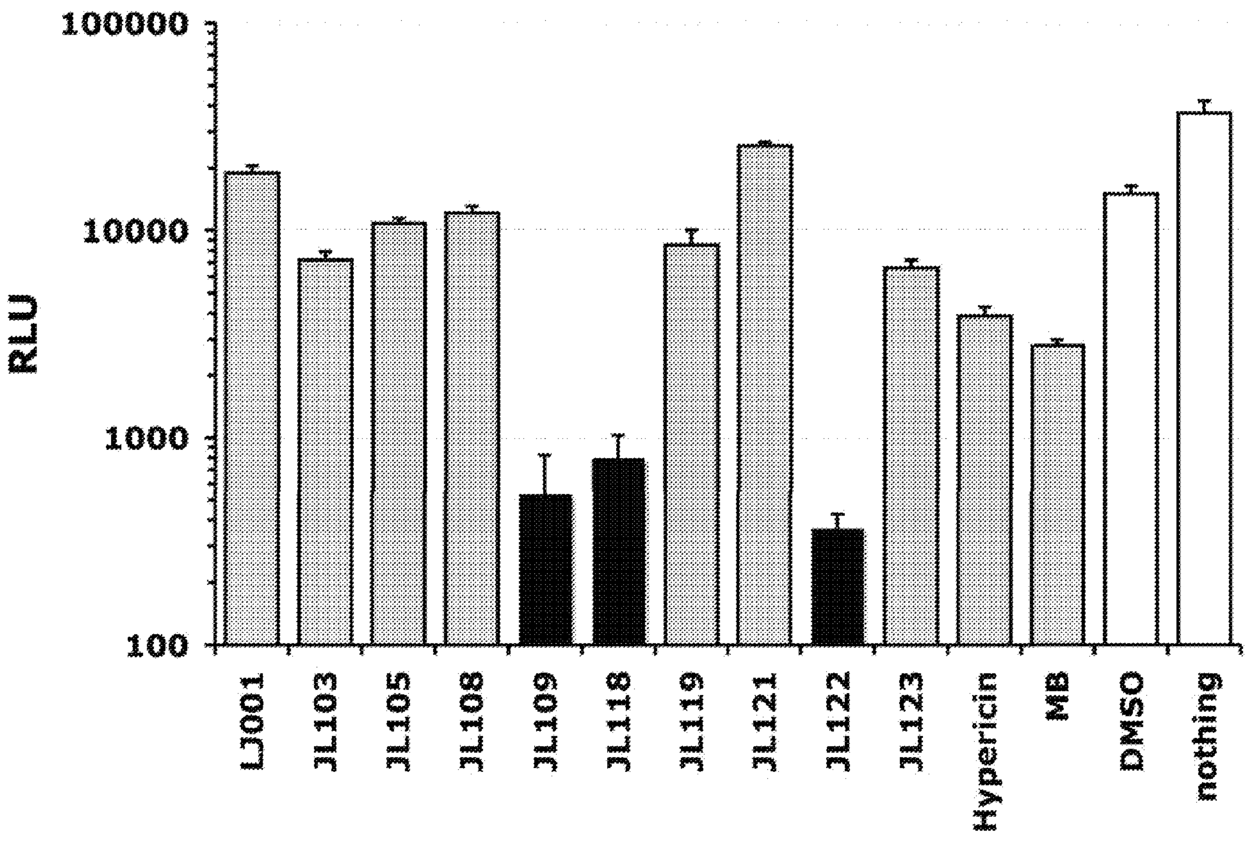
FIG. 4 shows HIV inactivation by several compounds of the present invention in packed red blood cells (RBC) at a hematocrit of 80%. Packed RBC spiked with HIV (IIIB) were treated for 1 h with 100 μM of the indicated compound. After treatment, the serum was used to infect the reporter cells TZM-BL. At 48 h after infection, luciferase expression was measured in cell lysates (RLU).

The disclosed compounds, including compound 2 (and perhaps analogues thereof) can be used to decontaminate blood products containing red blood cells (RBC) at various hematocrit (Hct) levels (see FIG. 4, HIV inactivation at a Hct of 80% by various selected compounds). Note that Hct 50% and 80% mimic RBC concentration in whole blood and in standard donor blood units, respectively.

Expired red blood cells (RBC) from the blood bank were spiked with HIV at a final hematocrit (Hct) of approximately 80% and treated with 100 μM of selected compounds for 1 h under white light on a shaker at 120 rpm. Cells were then centrifuged and the supernatant used to infect reporter TZM-BL cells. At 48 h post-infection, cells were lysed and the luciferase activity in the lysate measured (see FIG. 4). While LJ001 is unable to inactivate HIV at this concentration in an 80% Hct, some derivatives of compound 2 are able to inactivate HIV. Indeed, the compounds JL109, JL118 and JL122 all dramatically decrease the luciferase activity to near-background levels, indicating a dramatic reduction of infectious HIV particles in the packed RBC. Of note, these compounds also appear more effective in these conditions than the well-described and commonly used photosensitizers Hypericin and Methylene Blue (MB). Without being bound by a particular theory, it is believed that the effective compounds absorb at wavelengths that are higher than the one of the hemoglobin contained in red blood cells and thus can be excited by the light provided and generate singlet oxygen, triggering the inactivation of the virus. However, other mechanisms may be implied as both Hypericin and MB also have absorption peaks at wavelengths higher than 600 nm.

Example 6

Anti-Parasitic Activity Tested with *Toxoplasma gondii*

Attachment and invasion were assessed as described by Wetzel D M, et al. (J Cell Sci. 2004 Nov. 15; 117(Pt 24):5739-48. Epub 2004 Oct. 26.). Parasites were pelleted at 2500 rpm in a tabletop clinical centrifuge and washed in PBS. Equal numbers of parasites were resuspended in DMEM and compounds added to 10 μM with the DMSO control at 1%. Parasites were incubated in the presence of drug on ice for 15 min, then allowed to settle on coverslips of confluent HFFs on ice for 15 min. After being allowed to settle the cold media was changed out for warm media and parasites were allowed to invade at 37° C. for 1 hour, after which, coverslips were rinsed with ice cold PBS and fixed. Two color staining to discriminate between intracellular and extracellular parasites was as described by Straub, K. W., et al. (PLoS Pathog. 2011 March; 7(3):e1002007. Epub 2011 Mar. 10) Five random fields were counted on each coverslip and each experiment was done in triplicate. Results were normalized to DMSO control.

JL102, 103 and 107 inhibited parasite attachment and invasion with similar efficiency as LJ001 although variations in efficacy were observed. Preliminary results suggest JL107 has most potent inhibition of parasite attachment and invasion.

REFERENCES

[1] Wolf, M. C.; Freiberg, A. N.; Zhang, T.; Akyol-Ataman, Z.; Grock, A.; Hong, P. W.; Li, J.; Watson, N. F.; Fang, A. Q.; Aguilar, H. C.; Porotto, M.; Honko, A. N.; Damoiseaux, R.; Miller, J. P.; Woodson, S. E.; Chantasirivisal, S.; Fontanes, V.; Negrete, O. A.; Krogstad, P.; Dasgupta, A.; Moscona, A.; Hensley, L. E.; Whelan, S. P.; Faull, K. F.; Holbrook, M. R.; Jung, M. E.; Lee, B. A broad-spectrum antiviral targeting entry of enveloped viruses. *Proc Natl Acad Sci USA,* 2010, 7, 3157-62.

[2] Parker, W. B. Metabolism and antiviral activity of ribavirin. *Virus Res,* 2005, 2, 165-71.

The description of the aspects of the invention has been presented for the purpose of illustration; it is not intended to be exhaustive or to limit the invention to the precise forms disclosed. Persons skilled in the relevant art can appreciate that many modifications and variations are possible in light of the above teachings. It should be noted that the language used in the specification has been principally selected for readability and instructional purposes, and it may not have been selected to delineate or circumscribe the inventive subject matter. Accordingly, the disclosure of the aspects of the invention is intended to be illustrative, but not limiting, of the scope of the invention.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

It must be noted that, as used in the specification, the singular forms "a," "an" and "the" include plural referents unless the context clearly dictates otherwise.

All publications, references, issued patents and patent applications cited within the body of the specification are hereby incorporated by reference in their entirety, for all purposes.

What is claimed is:

1. A compound according to formula Ia or a pharmaceutically acceptable salt thereof, (Ia)

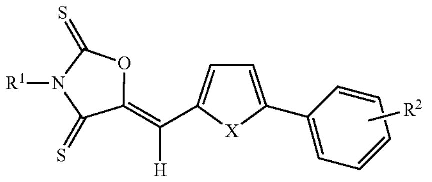

wherein $R^1$ is H, $C_1$-$C_6$ alkyl, $C_2$-$C_6$ alkenyl, $C_2$-$C_6$ alkynyl, $C_1$-$C_6$ alkoxy, $C_3$-$C_6$ aryl, $C_3$-$C_6$ heteroaryl, $C_3$-$C_6$ cycloalkyl, or $C_3$-$C_6$ heterocycloalkyl, each optionally substituted with halo, —$NO_2$, —$CF_3$, —CN, —$OR^3$, —$SR^3$, —$C(O)R^3$, —$NHC(O)R^3$, —$C(O)OR^3$, —$OC(O)R^3$, —$NR^4R^5$, —$C(O)NR^4R^5$, —$NHR^3C(O)NR^4R^5$, or —$SO_2NR^4R^5$;

$R^2$ represents one or more substituents independently selected from —$OR^3$, —$SR^3$, and —$NR^4R^5$;

$R^3$, $R^4$, and $R^5$ are independently H, $C_1$-$C_6$ alkyl, $C_2$-$C_6$ alkenyl, or $C_2$-$C_6$ alkynyl; and X is O, N, S, NH, or $NR^3$.

2. The compound claim 1, wherein $R^1$ is $C_1$-$C_6$ alkyl.

3. A pharmaceutical composition comprising the compound of claim 1 and at least one pharmaceutically acceptable excipient.

4. The pharmaceutical composition of claim 3, wherein the composition is suitable as a topical formulation.

5. The pharmaceutical composition of claim 4, which is in the form of a patch, an ointment, a cream, a lotion, a drop, a spray, or an aerosol.

6. The pharmaceutical composition of claim 4, which is in the form of a liposomal formulation.

7. The compound of claim 1 having formula:

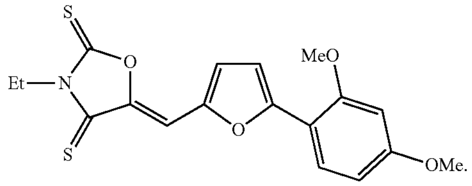 [SMILES: CCN1C(=S)O/C(=C\c2ccc(-c3ccc(OC)cc3OC)o2)C1=S]

8. The compound of claim 1 having formula:

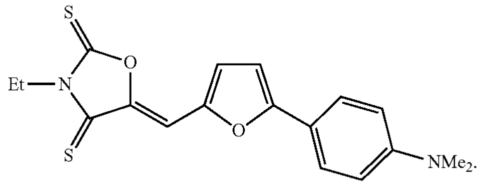 [SMILES: CCN1C(=S)O/C(=C\c2ccc(-c3ccc(N(C)C)cc3)o2)C1=S]

9. The compound of claim 1 having formula:

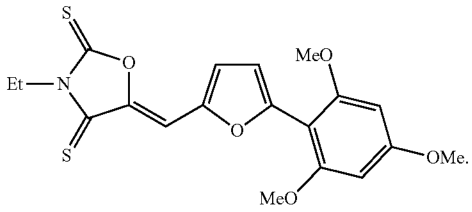 [SMILES: CCN1C(=S)O/C(=C\c2ccc(-c3c(OC)cc(OC)cc3OC)o2)C1=S]

* * * * *

UNITED STATES PATENT AND TRADEMARK OFFICE

CERTIFICATE OF CORRECTION

PATENT NO. : 9,139,575 B2
APPLICATION NO. : 13/640732
DATED : September 22, 2015
INVENTOR(S) : Benhur Lee et al.

It is certified that error appears in the above-identified patent and that said Letters Patent is hereby corrected as shown below:

IN THE SPECIFICATION

Column 1, lines 14-17 under STATEMENT OF GOVERNMENT SUPPORT please delete:

"This invention was made with Government support of Grant Nos. AI064616 AI069317 AI 070495 and AI 082100, awarded by the National Institutes of Health. The Government has certain rights in this invention."

and replace with:

--This invention was made with Government support under AI064616, AI69317, AI070495, and AI082100, awarded by National Institutes of Health. The Government has certain rights in the invention.--

Signed and Sealed this
Twenty-second Day of March, 2016

Michelle K. Lee
*Director of the United States Patent and Trademark Office*